(12) United States Patent
Muller et al.

(10) Patent No.: US 6,265,185 B1
(45) Date of Patent: Jul. 24, 2001

(54) YEAST PROMOTERS SUITABLE FOR EXPRESSION CLONING IN YEAST AND HETEROLOGOUS EXPRESSION OF PROTEINS IN YEAST

(75) Inventors: Sven Muller, Copenhagen; Henrik Dalbøge, Virum, both of (DK)

(73) Assignee: Novozymes A/S Patents, Bagsuaerd (DK)

( * ) Notice: Subject to any disclaimer, the term of this patent is extended or adjusted under 35 U.S.C. 154(b) by 0 days.

(21) Appl. No.: 09/174,768

(22) Filed: Oct. 19, 1998

Related U.S. Application Data

(63) Continuation of application No. PCT/DK97/00232, filed on May 21, 1997.

(30) Foreign Application Priority Data

May 21, 1996 (DK) .................................................. 0589/96

(51) Int. Cl.[7] ...................................................... C12P 21/06
(52) U.S. Cl. .......................... 435/69.1; 435/440; 435/483; 435/254.11; 435/254.2; 435/320.1; 536/24.1
(58) Field of Search .................................... 435/69.1, 440, 435/483, 254.11, 254.2, 320.1; 536/24.1

(56) References Cited

FOREIGN PATENT DOCUMENTS

| 0 220 864 A1 | 5/1987 | (EP) . |
|---|---|---|
| 0 220 864 B1 | 5/1987 | (EP) . |
| 0 402 226 | 12/1990 | (EP) . |
| WO 93/11249 | 6/1993 | (WO) . |
| WO 95/06739 | 3/1995 | (WO) . |

OTHER PUBLICATIONS

Dalboge et al., Mol Gen Genet, vol. 243, pp. 253–260 (1994).

*Primary Examiner*—Remy Yucel
(74) *Attorney, Agent, or Firm*—Jason I. Garbell, Esq.; Elias Lambiris, Esq.

(57) ABSTRACT

Novel yeast promoters for either EF1-alpha protein or ribosomal protein S7 gene suitable for expression cloning in yeast and heterologous expression of proteins in yeast. The yeast promoters are preferably active in the pH range 4–11 without peptone and obtained from the yeast strain *Yarrowia lipolytica*.

15 Claims, 14 Drawing Sheets

Figure 1A:
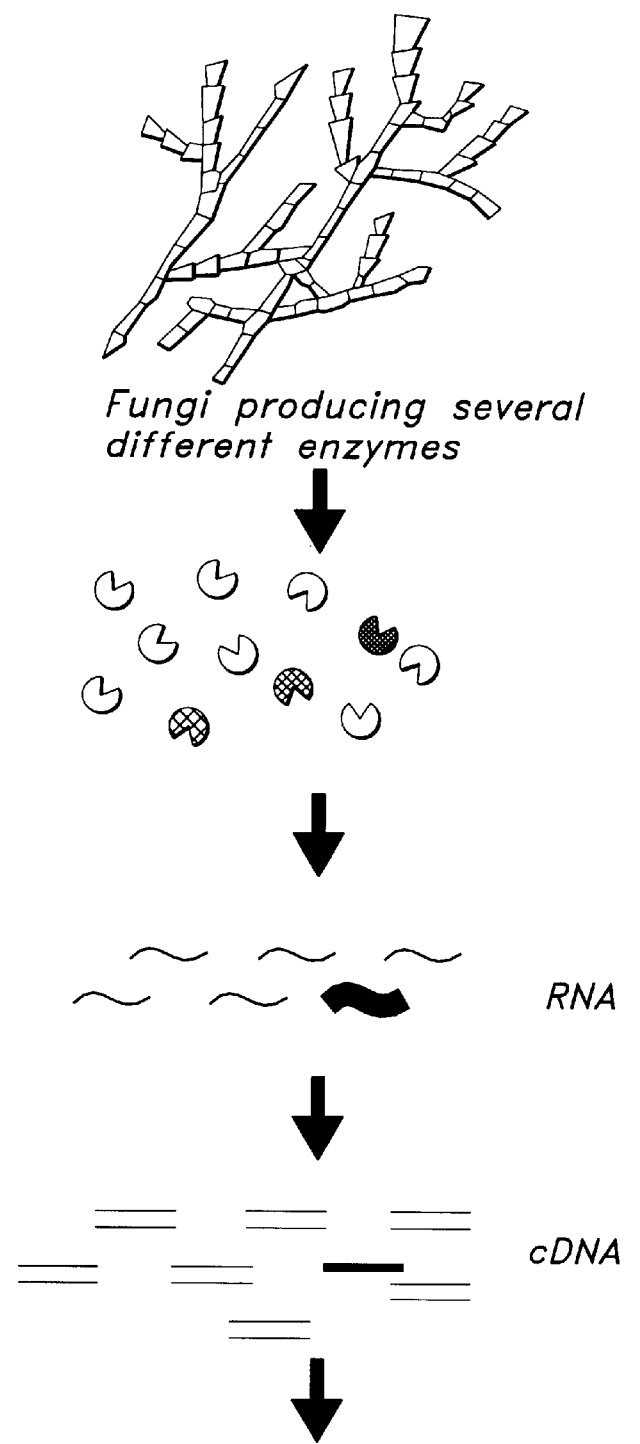

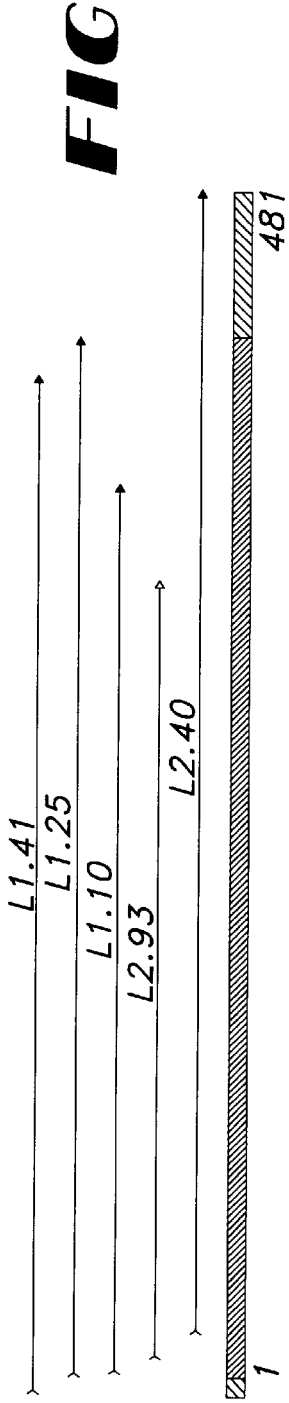
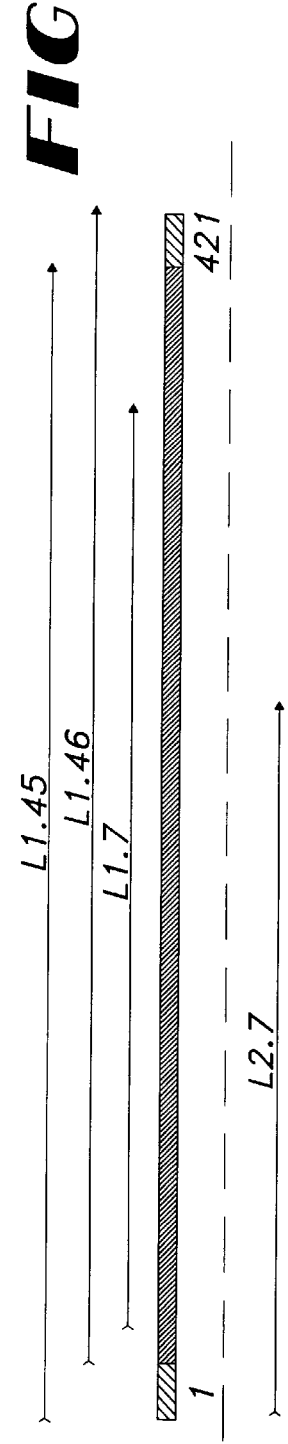
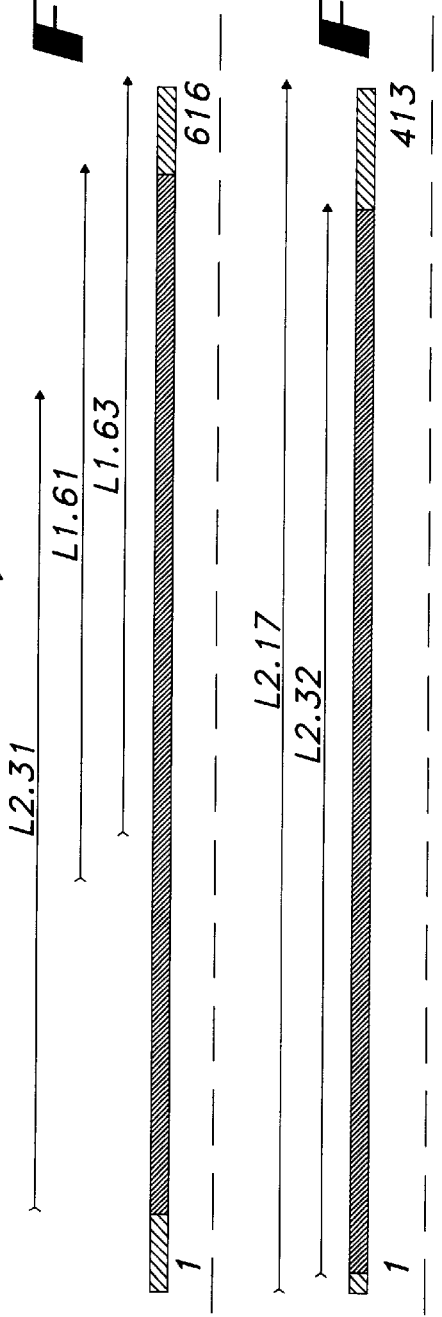

```
AGAGACCCGGGTTGGGGGCGTATTTGTGTCCCCAAAAAACAGCCCCCAATTGCCCCAATTGACCCCA  ÷333
GTAGCGGGCCCAACCCCGCGAGAGCCCCCCTTCACCCCCACATATCAAACCTCCCCCGGTTCCCACACTTGCCCGT  ÷259
TAAGGGCGTAGGGTACTGCAGTCTCGGAATCTACGCTTGTTCAGACTTTGTACTAGTTTCTTTGTCTGGCCATCC  ÷185
GGGTAACCCCATGCCGGGACGCAAAATAGACTACTGAAAATTTTTTGCTTTGTGGTTGGGACTTTAGCCAAGGGT  ÷111
ATAAAAGACCACCGTCCCCGAATTACCTTTCCCTTTCTCTCTCTCCCTTGTCAACTCACACCCGAAATCG  ÷37
TTAAGCATTTCCTTCTGAGTATAAGAATCATTCAAAATG  3
```

FIG 6

```
ATCGTTAAGCATTTCCTTCTGAGTATAAGAATCATTCAAAATGGGAAAGGAAAAGACTCACGTTAACCTCGTTGTCATCGGTCACGTCGA  90
                                  M  G  K  E  K  T  H  V  N  L  V  V  I  G  H  V  D
TGCCGGTAAGTCCACCACCACTGGTCACCTTATCTACAAGTGCGGTGGTATCGATAAGCGAACCATCGAGAAGTTCGAGAAGGAGGCCGA  180
 A  G  K  S  T  T  T  G  H  L  I  Y  K  C  G  G  I  D  K  R  T  I  E  K  F  E  K  E  A  D
CGAGCTTGGAAAGGGTTCTTTCAAGTACGCTTGGGTTCTTGACAAGCTTAAGGCTGAGCGAGAGCGAGGTATCACCATTGATATTGCTCT  270
  E  L  G  K  G  S  F  K  Y  A  W  V  L  D  K  L  K  A  E  R  E  R  G  I  T  I  D  I  A  L
CTGGAAGTTCCAGACCCCTAAGTACTACGTCACCGTTATTGATGCTCCCGGTCACCGAGATTTCATCAAGAACATGATCACCGGTACCTC  360
  W  K  F  Q  T  P  K  Y  Y  V  T  V  I  D  A  P  G  H  R  D  F  I  K  N  M  I  T  G  T  S
CCAGGCCGACTGTGCCATCCTCATCATTGCTGGTGGTGTTGGTGAGTTCGAGGCTGGTATCTCCAAGGACGGTCAGACCCGAGAGCACGC  450
  Q  A  D  C  A  I  L  I  I  A  G  G  V  G  E  F  E  A  G  I  S  K  D  G  Q  T  R  E  H  A
TCTGCTCGCTTTCACCCTCGGTGTCAAGCAGCTGATTGTTGCCATCAACAAGATGGACTCCGTCAAGTGGTCTCAGGATCGATACAACGA  540
   L  L  A  F  T  L  G  V  K  Q  L  I  V  A  I  N  K  M  D  S  V  K  W  S  Q  D  R  Y  N  E
GATCTGCAAGGAGACCGCCAACTTCGTCAAGAAGGTTGGTTACAACCCTAAGTCTGTCCCCTTTGTCCCTATTTCCGGATGGAACGGTGA  630
   I  C  K  E  T  A  N  F  V  K  K  V  G  Y  N  P  K  S  V  P  F  V  P  I  S  G  W  N  G  D
CAACATGATTGAGGCCTCCACCAACTGTGACTGGTACAAGGGCTGGACCAAGGAGACCAAGGCCGGTGAGGTCAAGGGTAAGACCCTCCT  720
  N  M  I  E  A  S  T  N  C  D  W  Y  K  G  W  T  K  E  T  K  A  G  E  V  K  G  K  T  L  L
TGAGGCCATTGACGCCATTGAGCCCCCCGTGCGACCCTCCGACAAGCCCTCCGACTTCCTCTCCAGGATGTCTACAAGATCGGTGGTAT  810
  E  A  I  D  A  I  E  P  P  V  R  P  S  D  K  P  L  R  L  P  L  Q  D  V  Y  K  I  G  G  I
CGGCACAGTGCCCGTTGGCCGAGTCGAGACCGGTGTTATCAAGGCCGGTATGGTTGTTACCTTCGCTCCCGCCAACGTGACCACTGAGGT  900
  G  T  V  P  V  G  R  V  E  T  G  V  I  K  A  G  M  V  V  T  F  A  P  A  N  V  T  T  E  V
CAAGTCTGTCGAGATGCACCACGAGATCCTCCCCGACGGAGGTTTCCCCGGTGACAACGTTGGCTTCAACGTCAAGAACGTTTCCGTCAA  990
  K  S  V  E  M  H  H  E  I  L  P  D  G  G  F  P  G  D  N  V  G  F  N  V  K  N  V  S  V  K
GGATATCCGACGAGGTAACGTTGCCGGTGACTCCAAGAACGACCCCCCTAATGGCTGCGACTCTTTCAACGCTCAGGTCATTGTTCTTAA  1080
  D  I  R  R  G  N  V  A  G  D  S  K  N  D  P  P  N  G  C  D  S  F  N  A  Q  V  I  V  L  N
CCACCCCGGTCAGATCGGTGCTGGTTACGCTCCCGTTCTTGATTGCCACACTGCCCACATTGCCTGCAAGTTCGACACCCTGATCGTTAA  1170
  H  P  G  Q  I  G  A  G  Y  A  P  V  L  D  C  H  T  A  H  I  A  C  K  F  D  T  L  I  E  K
GATCGACCGACGAACCGGTAAGAAGATGGAGGACTCCCCCAAGTTCCATCAAGTCTGGTGATGCCGCCATTGTCAAGATGGTCCCCTCAA  1260
   I  D  R  R  T  G  K  K  M  E  D  S  P  K  F  I  K  S  G  D  A  A  I  V  K  M  V  P  S  K
GCCCATGTGTGTTGAGGCCTTCACTGAGTACCCCCCTCTTGGTCGATTCGCCGTCCGAGACATGCGACAGACCGTTGCTGTCGGTGTCAT  1350
  P  M  C  V  E  A  F  T  E  Y  P  P  L  G  R  F  A  V  R  D  M  R  Q  T  V  A  V  G  V  I
CAAGTCCGTCGAGAAGTCCGACAAGGCTGGTGGAAAGGTCACCAAGGCTGCCCAGAAGGCTGCCAAGAAATAAGCTGCTTGTACCTAGTG  1440
   K  S  V  E  K  S  D  K  A  G  G  K  V  T  K  A  A  Q  K  A  A  K  K
CAACCCCAGTTTGTTAAAAATTAGTAGTCAAAAACTTCTGAGTTAAAAAAAAAAAAAAAAA
```

FIG 7

BamHI
TCGACGGATCCACTTGTATGGCTCCAAGTTCAGTGTACCAAGTAGTTGGTGATGCAGGGAGGGATGTCTCTATC +687

CACCAATAATGAACTCATGGGCGAAATTGTTTCTGTTAAACACTCCAACTGTCGTTTAAATCTCATTCTCTTT +613

GCATTTGGACTCCATTCGCTTCCCGTTGGGCCATATAATCCATCGTAACGTACTTTAGATGGAAATTTAGTTACC +539

TGCTACTTGTCTCAACACCCCAACAGGGGCTGTTCGACAGAGGTAATAGAGCGTCAATGGGTTAATAAAAACAC +465

ACTGTCGATTTCACTCATTGTCTTTATGATATTACCTGTTTCCGCTGTTATCAATGCCGAGCATCGGTGTTAT +391

ATCTTCCACCCCAACTACTGCATTACTTAACTATTACCTCAACTATTTACACCCCGAATTGTACCTCCCAA +317

TAAGTAACTTTATTTCAACCATGGGACGAGAGCATCTCTGAGAACATCGATCTATCTCTGTCAATATTGCCCA +243
                                                                    ClaI

GAATCGTTCGAAAAAACACCAAAGGTTTACAGCGGCCATTATAAATATAAATTCGTTGTCAATTCCCCCGCA +169

ATGTCTGTTGAAATCTCATTTGAGACCTTCCAACATTACCCTCTCTCCCGTCTGGTCACATGACGTGACTGCT +95

TCTTCCCAAAACGAACACTCTCCCCCCGTCAGTGAAAAGTATACATCCGACCTCCCAAATCTTTTC +21

TTCACTCAACAACACAACAAAAATGGCCCGAGGACCGTGAGTATCCCCCACCCCCGATCAGATGAGGCACAGACC 54

AGGCTAGCCCCATCGCTTTTAGAAGAAGGATAAGGGCTTCTGGGTGTGTCAAGAGGAGATGATGACGAGAAGC 128

AAAGAGCTTCGACTCAGTCGCCCTCTGCCCCACGAACTAAACTAACGCCAG    CAAGAAGCATCTC → 192

*FIG 8*

AAATGGCCCGAGGACCCAAGAAGCATCTCAAGGCGACTCGCAGCTCCCTCCCACTGGATGCTGGACAAGCTGTCCGGCACCTACGCTCCCC 90
M A R G P K K H L K R L A A P S H W M L D K L S G T Y A P

GATCGCTCTGCCGGTCCCCACAAGCTGCGAGAGTCTCTGCCTCTCGTCATCTTCCTGCGAAACCGTCTCAAGTACGCCCTGAACGGCCGAG 180
R S S A G P H K L R E S L P L V I F L R N R L K Y A L N G R

AGGTTAACGCCATTCTCATGCAGCGACTGGTCAAGGTCGACGGCAAGGTCCGAACCGACTCCACTTTCCCCGCTGGCTTCATGGATGTCA 270
E V N A I L M Q R L V K V D G K V R T D S T F P A G F M D V

TCCAGCTCGAGAAGACCGGCGAGAACTTCCGACTTGTCTACGACGTCAAGGGCCGATTTGCCGTCCACCGAATCACCGATGAGGAGGGTG 360
I Q L E K T G E N F R L V Y D V K G R F A V H R I T D E E A

CTTACAAGCTCGGCAAGGTCAAGCGAGTCCAGGTTGGCAAGAAGGGTATCCCCTACCTCGTCACCCACGACGGCCGAACCATCCGGTACC 450
A Y K L G K V K R V Q V G K K G I P Y L V T H D G R T I R Y

CCGACCCCTCTCATCAAGGTCAACGACACCGTCAAGATCGACCTGGCCACCGGCAAGATCACCTCTTTCGTCAAGTTTGAGAACGGTAACA 540
P D P L I K V N D T V K I D L A T G K I T S F V K F E N G N

TTGTCATGACCACCGGCCGAGGTCGAAACATGGGCCGAGTCGGCACCATCACCCACCGAGAGGCGACATGAGGGTGGCTTCGATATCGTCCACA 630
I V M T T G G R N M G R V G T I T H R E R H E G G F D I V H

TCAAGGACGCTCTTGACAACCAGTTTGTTACCCGACTCACTAACGTTTTCGTTATCGGTGAGGGCAACAGTCTCTCATCTCTCTGCCCA 720
I K D A L D N Q F V T R L T N V F V I G E G N K S L I S L P

AGGGCAAGGGTATCAAGCTCTCCATTGCTGAGGAGGCGGAGATGCCCGACGAGCCAAGCAGGAGTAAGTTCAGATTGGAACAACATTGGTTT 810
K G K G I K L S I A E E R D A R R A K Q E *

AGCTAAAAAAAAAGGATTCATGTTTAAAAAAAAAAAAAAAAAAAA

*FIG 9*

SEQUENCE LISTING

<160> NUMBER OF SEQ ID NOS: 6

<210> SEQ ID NO: 1
<211> LENGTH: 409
<212> TYPE: DNA
<213> ORGANISM: Yarrowia lipolytica

<400> SEQUENCE: 1

```
agagaccggg ttggcggcgt atttgtgtcc caaaaaacag ccccaattgc cccaattgac      60
cccaaattga cccagtagcg ggcccaaccc cggcgagagc cccccttcacc ccacatatca     120 aacctccccc ggttcccaca cttgccgtta agggcgtagg gtactgcagt ctggaatcta    180
cgcttgttca gactttgtac tagtttcttt gtctggccat ccgggtaacc catgccggac    240
gcaaaataga ctactgaaaa tttttttgct ttgtggttgg gactttagcc aagggtataa    300
aagaccaccg tccccgaatt acctttcctc ttcttttctc tctctccttg tcaactcaca    360
cccgaaatcg ttaagcattt ccttctgagt ataagaatca ttcaaaatg                409
```

<210> SEQ ID NO: 2
<211> LENGTH: 952
<212> TYPE: DNA
<213> ORGANISM: Yarrowia lipolytica

<400> SEQUENCE: 2

```
tcgacggatc cacttgtatg gctccaagtt cagtgtacca agtagttggt gatgcaggga      60
gggatgtctc tatccaccaa taatgaactc atgggcgaaa ttgtttctgt taaacactcc     120
aactgtcgtt ttaaatctca ttctctttgc atttggactc cattcgcttc cgttgggcca    180
tataatccat cgtaacgtac tttagatgga aatttagtta cctgctactt gtctcaacac    240
```

-continued

```
cccaacaggg gctgttcgac agaggtaata gagcgtcaat gggttaataa aaacacactg      300
tcgattttca ctcattgtct ttatgatatt acctgttttc cgctgttatc aatgccgagc      360
atcgtgttat atcttccacc ccaactactt gcatttactt aactattacc tcaactattt      420
acaccccgaa ttgttacctc ccaataagta actttatttc aaccaatggg acgagagcat      480
ctctgagaac atcgatctat ctctgtcaat attgcccaga atcgttcgaa aaaaacacc       540 aaaaggttta cagcgccatt ataaatataa attcgttgtc aattccccg caatgtctgt       600 tgaaatctca ttttgagacc ttccaacatt accctctctc ccgtctggtc acatgacgtg      660
actgcttctt cccaaaacga acactcccaa ctcttcccccc cgtcagtga aagtataca       720 tccgacctcc aaatcttttc ttcactcaac aaacacaaaa atggcccgag accgtgagt       780 atcccccacc ccccgatcag atgaggcaca gaccaggcta gcccatcgct tttagaagaa      840
ggataagggc tgttctgggt gtgtcaagag gagatgatga cgagaagcaa agagcttcga      900
ctcagtcgcc tctgccccca cgaactaaac taacgccagc aagaagcatc tc             952

<210> SEQ ID NO: 3
<211> LENGTH: 1500
<212> TYPE: DNA
<213> ORGANISM: EF-1alpha
<220> FEATURE:
<221> NAME/KEY: CDS
<222> LOCATION: (41)...(1420)

<400> SEQUENCE: 3
atcgttaagc atttccttct gagtataaga atcattcaaa atg gga aag gaa aag       55
                                              Met Gly Lys Glu Lys
                                                1               5 act cac gtt aac ctc gtt gtc atc ggt cac gtc gat gcc ggt aag tcc      103
Thr His Val Asn Leu Val Val Ile Gly His Val Asp Ala Gly Lys Ser
            10                  15                  20 acc acc act ggt cac ctt atc tac aag tgc ggt ggt atc gat aag cga      151
Thr Thr Thr Gly His Leu Ile Tyr Lys Cys Gly Gly Ile Asp Lys Arg
        25                  30                  35 acc atc gag aag ttc gag aag gag gcc gac gag ctt gga aag ggt tct      199
Thr Ile Glu Lys Phe Glu Lys Glu Ala Asp Glu Leu Gly Lys Gly Ser
    40                  45                  50 ttc aag tac gct tgg gtt ctt gac aag ctt aag gct gag cga gag cga      247
Phe Lys Tyr Ala Trp Val Leu Asp Lys Leu Lys Ala Glu Arg Glu Arg
55                  60                  65 ggt atc acc att gat att gct ctc tgg aag ttc cag acc cct aag tac      295
Gly Ile Thr Ile Asp Ile Ala Leu Trp Lys Phe Gln Thr Pro Lys Tyr
    70                  75                  80                  85 tac gtc acc gtt att gat gct ccc ggt cac cga gat ttc atc aag aac      343
Tyr Val Thr Val Ile Asp Ala Pro Gly His Arg Asp Phe Ile Lys Asn
            90                  95                  100 atg atc acc ggt acc tcc cag gcc gac tgt gcc atc ctc atc att gct      391
Met Ile Thr Gly Thr Ser Gln Ala Asp Cys Ala Ile Leu Ile Ile Ala
        105                 110                 115 ggt ggt gtt ggt gag ttc gag gct ggt atc tcc aag gac ggt cag acc      439
Gly Gly Val Gly Glu Phe Glu Ala Gly Ile Ser Lys Asp Gly Gln Thr
    120                 125                 130 cga gag cac gct ctg ctc gct ttc acc ctc ggt gtc aag cag ctg att      487
Arg Glu His Ala Leu Leu Ala Phe Thr Leu Gly Val Lys Gln Leu Ile
135                 140                 145 gtt gcc atc aac aag atg gac tcc gtc aag tgg tct cag gat cga tac      535
Val Ala Ile Asn Lys Met Asp Ser Val Lys Trp Ser Gln Asp Arg Tyr
            150                 155                 160                 165
```

```
aac gag atc tgc aag gag acc gcc aac ttc gtc aag aag gtt ggt tac    583
Asn Glu Ile Cys Lys Glu Thr Ala Asn Phe Val Lys Lys Val Gly Tyr
            170                 175                 180 aac cct aag tct gtc ccc ttt gtc cct att tcc gga tgg aac ggt gac    631
Asn Pro Lys Ser Val Pro Phe Val Pro Ile Ser Gly Trp Asn Gly Asp
        185                 190                 195 aac atg att gag gcc tcc acc aac tgt gac tgg tac aag ggc tgg acc    679
Asn Met Ile Glu Ala Ser Thr Asn Cys Asp Trp Tyr Lys Gly Trp Thr
        200                 205                 210 aag gag acc aag gcc ggt gag gtc aag ggt aag acc ctc ctt gag gcc    727
Lys Glu Thr Lys Ala Gly Glu Val Lys Gly Lys Thr Leu Leu Glu Ala
        215                 220                 225 att gac gcc att gag ccc ccc gtg cga ccc tcc gac aag ccc ctc cga    775
Ile Asp Ala Ile Glu Pro Pro Val Arg Pro Ser Asp Lys Pro Leu Arg
230                 235                 240                 245 ctt cct ctc cag gat gtc tac aag atc ggt ggt atc ggc aca gtg ccc    823
Leu Pro Leu Gln Asp Val Tyr Lys Ile Gly Gly Ile Gly Thr Val Pro
            250                 255                 260 gtt ggc cga gtc gag acc ggt gtt atc aag gcc ggt atg gtt gtt acc    871
Val Gly Arg Val Glu Thr Gly Val Ile Lys Ala Gly Met Val Val Thr
        265                 270                 275 ttc gct ccc gcc aac gtg acc act gag gtc aag tct gtc gag atg cac    919
Phe Ala Pro Ala Asn Val Thr Thr Glu Val Lys Ser Val Glu Met His
        280                 285                 290 cac gag atc ctc ccc gac gga ggt ttc ccc ggt gac aac gtt ggc ttc    967
His Glu Ile Leu Pro Asp Gly Gly Phe Pro Gly Asp Asn Val Gly Phe
        295                 300                 305 aac gtc aag aac gtt tcc gtc aag gat atc cga cga ggt aac gtt gcc   1015
Asn Val Lys Asn Val Ser Val Lys Asp Ile Arg Arg Gly Asn Val Ala
310                 315                 320                 325 ggt gac tcc aag aac gac ccc cct aat ggc tgc gac tct ttc aac gct   1063
Gly Asp Ser Lys Asn Asp Pro Pro Asn Gly Cys Asp Ser Phe Asn Ala
            330                 335                 340 cag gtc att gtt ctt aac cac ccc ggt cag atc ggt gct ggt tac gct   1111
Gln Val Ile Val Leu Asn His Pro Gly Gln Ile Gly Ala Gly Tyr Ala
        345                 350                 355 ccc gtt ctt gat tgc cac act gcc cac att gcc tgc aag ttc gac acc   1159
Pro Val Leu Asp Cys His Thr Ala His Ile Ala Cys Lys Phe Asp Thr
        360                 365                 370 ctg atc gag aag atc gac cga cga acc ggt aag aag atg gag gac tcc   1207
Leu Ile Glu Lys Ile Asp Arg Arg Thr Gly Lys Lys Met Glu Asp Ser
375                 380                 385 ccc aag ttc atc aag tct ggt gat gcc gcc att gtc aag atg gtc ccc   1255
Pro Lys Phe Ile Lys Ser Gly Asp Ala Ala Ile Val Lys Met Val Pro
390                 395                 400                 405 tcc aag ccc atg tgt gtt gag gcc ttc act gag tac ccc cct ctt ggt   1303
Ser Lys Pro Met Cys Val Glu Ala Phe Thr Glu Tyr Pro Pro Leu Gly
            410                 415                 420 cga ttc gcc gtc cga gac atg cga cag acc gtt gct gtc ggt gtc atc   1351
Arg Phe Ala Val Arg Asp Met Arg Gln Thr Val Ala Val Gly Val Ile
        425                 430                 435 aag tcc gtc gag aag tcc gac aag gct ggt gga aag gtc acc aag gct   1399
Lys Ser Val Glu Lys Ser Asp Lys Ala Gly Gly Lys Val Thr Lys Ala
        440                 445                 450 gcc cag aag gct gcc aag aaa taagctgctt gtacctagtg caaccccagt      1450
Ala Gln Lys Ala Ala Lys Lys
        455                 460 ttgttaaaaa ttagtagtca aaacttctg agttaaaaaa aaaaaaaaaa             1500
```

-continued

```
<210> SEQ ID NO: 4
<211> LENGTH: 460
<212> TYPE: PRT
<213> ORGANISM: EF-1alpha

<400> SEQUENCE: 4

Met Gly Lys Glu Lys Thr His Val Asn Leu Val Val Ile Gly His Val
 1               5                  10                  15

Asp Ala Gly Lys Ser Thr Thr Thr Gly His Leu Ile Tyr Lys Cys Gly
                20                  25                  30

Gly Ile Asp Lys Arg Thr Ile Glu Lys Phe Glu Lys Glu Ala Asp Glu
            35                  40                  45

Leu Gly Lys Gly Ser Phe Lys Tyr Ala Trp Val Leu Asp Lys Leu Lys
        50                  55                  60

Ala Glu Arg Glu Arg Gly Ile Thr Ile Asp Ile Ala Leu Trp Lys Phe
65                  70                  75                  80

Gln Thr Pro Lys Tyr Tyr Val Thr Val Ile Asp Ala Pro Gly His Arg
                85                  90                  95

Asp Phe Ile Lys Asn Met Ile Thr Gly Thr Ser Gln Ala Asp Cys Ala
            100                 105                 110

Ile Leu Ile Ile Ala Gly Gly Val Gly Glu Phe Glu Ala Gly Ile Ser
        115                 120                 125

Lys Asp Gly Gln Thr Arg Glu His Ala Leu Leu Ala Phe Thr Leu Gly
130                 135                 140

Val Lys Gln Leu Ile Val Ala Ile Asn Lys Met Asp Ser Val Lys Trp
145                 150                 155                 160

Ser Gln Asp Arg Tyr Asn Glu Ile Cys Lys Glu Thr Ala Asn Phe Val
                165                 170                 175

Lys Lys Val Gly Tyr Asn Pro Lys Ser Val Pro Phe Val Pro Ile Ser
            180                 185                 190

Gly Trp Asn Gly Asp Asn Met Ile Glu Ala Ser Thr Asn Cys Asp Trp
        195                 200                 205

Tyr Lys Gly Trp Thr Lys Glu Thr Lys Ala Gly Glu Val Lys Gly Lys
    210                 215                 220

Thr Leu Leu Glu Ala Ile Asp Ala Ile Glu Pro Pro Val Arg Pro Ser
225                 230                 235                 240

Asp Lys Pro Leu Arg Leu Pro Leu Gln Asp Val Tyr Lys Ile Gly Gly
                245                 250                 255

Ile Gly Thr Val Pro Val Gly Arg Val Glu Thr Gly Val Ile Lys Ala
            260                 265                 270

Gly Met Val Val Thr Phe Ala Pro Ala Asn Val Thr Thr Glu Val Lys
        275                 280                 285

Ser Val Glu Met His His Glu Ile Leu Pro Asp Gly Phe Pro Gly
290                 295                 300

Asp Asn Val Gly Phe Asn Val Lys Asn Val Ser Val Lys Asp Ile Arg
305                 310                 315                 320

Arg Gly Asn Val Ala Gly Asp Ser Lys Asn Asp Pro Pro Asn Gly Cys
                325                 330                 335

Asp Ser Phe Asn Ala Gln Val Ile Val Leu Asn His Pro Gly Gln Ile
            340                 345                 350

Gly Ala Gly Tyr Ala Pro Val Leu Asp Cys His Thr Ala His Ile Ala
        355                 360                 365

Cys Lys Phe Asp Thr Leu Ile Glu Lys Ile Asp Arg Arg Thr Gly Lys
    370                 375                 380
```

```
Lys Met Glu Asp Ser Pro Lys Phe Ile Lys Ser Gly Asp Ala Ala Ile
385                 390                 395                 400

Val Lys Met Val Pro Ser Lys Pro Met Cys Val Glu Ala Phe Thr Glu
            405                 410                 415

Tyr Pro Pro Leu Gly Arg Phe Ala Val Arg Asp Met Arg Gln Thr Val
            420                 425                 430

Ala Val Gly Val Ile Lys Ser Val Glu Lys Ser Asp Lys Ala Gly Gly
            435                 440                 445

Lys Val Thr Lys Ala Ala Gln Lys Ala Ala Lys Lys
    450                 455                 460

<210> SEQ ID NO: 5
<211> LENGTH: 853
<212> TYPE: DNA
<213> ORGANISM: Ribosomal Protein S7
<220> FEATURE:
<221> NAME/KEY: CDS
<222> LOCATION: (3)...(782)

<400> SEQUENCE: 5 aa atg gcc cga gga ccc aag aag cat ctc aag cga ctc gca gct ccc      47
   Met Ala Arg Gly Pro Lys Lys His Leu Lys Arg Leu Ala Ala Pro
   1               5                   10                  15 tcc cac tgg atg ctg gac aag ctg tcc ggc acc tac gct ccc cga tcg     95
Ser His Trp Met Leu Asp Lys Leu Ser Gly Thr Tyr Ala Pro Arg Ser
                20                  25                  30 tct gcc ggt ccc cac aag ctc cga gag tct ctg cct ctc gtc atc ttc    143
Ser Ala Gly Pro His Lys Leu Arg Glu Ser Leu Pro Leu Val Ile Phe
            35                  40                  45 ctg cga aac cgt ctc aag tac gcc ctg aac ggc cga gag gtt aac gcc    191
Leu Arg Asn Arg Leu Lys Tyr Ala Leu Asn Gly Arg Glu Val Asn Ala
        50                  55                  60 att ctc atg cag cga ctg gtc aag gtc gac ggc aag gtc cga acc gac    239
Ile Leu Met Gln Arg Leu Val Lys Val Asp Gly Lys Val Arg Thr Asp
    65                  70                  75 tcc act ttc ccc gct ggc ttc atg gat gtc atc cag ctc gag aag acc    287
Ser Thr Phe Pro Ala Gly Phe Met Asp Val Ile Gln Leu Glu Lys Thr
80                  85                  90                  95 ggc gag aac ttc cga ctt gtc tac gac gtc aag ggc cga ttt gcc gtc    335
Gly Glu Asn Phe Arg Leu Val Tyr Asp Val Lys Gly Arg Phe Ala Val
                100                 105                 110 cac cga atc acc gat gag gag gct gct tac aag ctc ggc aag gtc aag    383
His Arg Ile Thr Asp Glu Glu Ala Ala Tyr Lys Leu Gly Lys Val Lys
            115                 120                 125 cga gtc cag gtt ggc aag aag ggt atc ccc tac ctc gtc acc cac gac    431
Arg Val Gln Val Gly Lys Lys Gly Ile Pro Tyr Leu Val Thr His Asp
        130                 135                 140 ggc cga acc atc cgg tac ccc gac cct ctc atc aag gtc aac gac acc    479
Gly Arg Thr Ile Arg Tyr Pro Asp Pro Leu Ile Lys Val Asn Asp Thr
    145                 150                 155 gtc aag atc gac ctg gcc acc ggc aag atc acc tct ttc gtc aag ttt    527
Val Lys Ile Asp Leu Ala Thr Gly Lys Ile Thr Ser Phe Val Lys Phe
160                 165                 170                 175 gag aac ggt aac att gtc atg acc acc gga ggt cga aac atg ggc cga    575
Glu Asn Gly Asn Ile Val Met Thr Thr Gly Gly Arg Asn Met Gly Arg
                180                 185                 190 gtc ggc acc atc acc cac cga gag cga cat gag ggt ggc ttc gat atc    623
Val Gly Thr Ile Thr His Arg Glu Arg His Glu Gly Gly Phe Asp Ile
            195                 200                 205
```

```
gtc cac atc aag gac gct ctt gac aac cag ttt gtt acc cga ctc act    671
Val His Ile Lys Asp Ala Leu Asp Asn Gln Phe Val Thr Arg Leu Thr
        210                 215                 220 aac gtt ttc gtt atc ggt gag ggc aac aag tct ctc atc tct ctg ccc    719
Asn Val Phe Val Ile Gly Glu Gly Asn Lys Ser Leu Ile Ser Leu Pro
    225                 230                 235 aag ggc aag ggt atc aag ctc tcc att gct gag gag cga gat gcc cga    767
Lys Gly Lys Gly Ile Lys Leu Ser Ile Ala Glu Glu Arg Asp Ala Arg
240                 245                 250                 255 cga gcc aag cag gag taagttcaga ttggaacaac attggttag ctaaaaaaaa     822
Arg Ala Lys Gln Glu
                260 ggattcatgt ttaaaaaaaa aaaaaaaaaa a                                 853

<210> SEQ ID NO: 6
<211> LENGTH: 260
<212> TYPE: PRT
<213> ORGANISM: Yarrowia lipolytica

<400> SEQUENCE: 6

Met Ala Arg Gly Pro Lys Lys His Leu Lys Arg Leu Ala Ala Pro Ser
1               5                   10                  15

His Trp Met Leu Asp Lys Leu Ser Gly Thr Tyr Ala Pro Arg Ser Ser
            20                  25                  30

Ala Gly Pro His Lys Leu Arg Glu Ser Leu Pro Leu Val Ile Phe Leu
        35                  40                  45

Arg Asn Arg Leu Lys Tyr Ala Leu Asn Gly Arg Glu Val Asn Ala Ile
    50                  55                  60

Leu Met Gln Arg Leu Val Lys Val Asp Gly Lys Val Arg Thr Asp Ser
65                  70                  75                  80

Thr Phe Pro Ala Gly Phe Met Asp Val Ile Gln Leu Glu Lys Thr Gly
                85                  90                  95

Glu Asn Phe Arg Leu Val Tyr Asp Val Lys Gly Arg Phe Ala Val His
            100                 105                 110

Arg Ile Thr Asp Glu Glu Ala Ala Tyr Lys Leu Gly Lys Val Lys Arg
        115                 120                 125

Val Gln Val Gly Lys Lys Gly Ile Pro Tyr Leu Val Thr His Asp Gly
    130                 135                 140

Arg Thr Ile Arg Tyr Pro Asp Pro Leu Ile Lys Val Asn Asp Thr Val
145                 150                 155                 160

Lys Ile Asp Leu Ala Thr Gly Lys Ile Thr Ser Phe Val Lys Phe Glu
                165                 170                 175

Asn Gly Asn Ile Val Met Thr Thr Gly Gly Arg Asn Met Gly Arg Val
            180                 185                 190

Gly Thr Ile Thr His Arg Glu Arg His Glu Gly Gly Phe Asp Ile Val
        195                 200                 205

His Ile Lys Asp Ala Leu Asp Asn Gln Phe Val Thr Arg Leu Thr Asn
    210                 215                 220

Val Phe Val Ile Gly Glu Gly Asn Lys Ser Leu Ile Ser Leu Pro Lys
225                 230                 235                 240

Gly Lys Gly Ile Lys Leu Ser Ile Ala Glu Glu Arg Asp Ala Arg Arg
                245                 250                 255

Ala Lys Gln Glu
            260
```

US 6,265,185 B1

YEAST PROMOTERS SUITABLE FOR EXPRESSION CLONING IN YEAST AND HETEROLOGOUS EXPRESSION OF PROTEINS IN YEAST

CROSS-REFERENCE TO RELATED APPLICATIONS

This application is a continuation of application No. PCT/DK97/00232 filed on May 21, 1997 and claims priority under 35 U.S.C. 119 of Danish application no. 0589/96 filed May 21, 1996, the contents of which are fully incorporated herein by reference.

FIELD OF INVENTION

Background of the Invention

The advent of recombinant DNA techniques has made it possible to select single protein components with interesting properties and produce them on a large scale. This represents an improvement over the previously employed production process using micro-organisms isolated from nature and producing a mixture of proteins which would either be used as such or separated after the production step. However, the conventional cloning techniques have the drawback that each protein component has to be purified and characterised by its (partial) amino acid sequence before it is possible to prepare synthetic oligonucleotide probes for hybridisation experiments. Since this is a rather time-consuming process, the cloning of novel proteins might be considerably expedited by using a screening method involving selecting clones expressing a desired protein activity, i.e. expression cloning.

Recently, a novel method for cloning of fungal enzyme genes by expression cloning in yeast was developed by Dalbøge and Heldt-Hansen (A novel method for efficient expression cloning of fungal enzyme genes. Mol. Gen. Genet. 243: 253–260. (1994), WO 93/11249).

This expression cloning technique combines the ability of a yeast strain (e.g. *Saccharomyces cerevisiae*) to express heterologous genes with the utilisation of sensitive enzyme plate assays. The principle in expression cloning is outlined in FIG. 1.

This method makes it possible to clone enzyme genes independently of knowledge of the amino acid sequence and has proven successful in cloning a number of new enzymes.

Even though the above described method already have proven successful, there is still room for improvement.

Improvement of the expression cloning technique can be done by identifying new improved promoters, e.g. to increase expression of naturally low expressed enzymes and thereby facilitating the subsequent screening.

EP 220864 describes a *Yarrowia lipolytica* yeast promoter XPR2. The XPR2 yeast promoter is only active at pH above 6.0 on media lacking preferred carbon and nitrogen sources and full induction requires high levels of peptone in the culture medium (Ogrydziak, D. M., Demain, A. L., and Tannenbaum, S. R. (1977) Biochim. Biophys. Acta. 497: 525–538.; Ogrydziak, D. M. and Scharf, S. J. (1982). Gen. Microbiol. 128: 1225–1234.).

The demand for pH above 6.0 in the medium makes it difficult to screen directly for secreted enzymes that are active only in an acidic environment.

Therefore, an object of the present invention, is to provide new improved yeast promoters, especially for use in expression cloning in yeast, but also for heterologous expression of a desired polypeptide in an expression system of choice.

SUMMARY OF THE INVENTION

The present invention is based on the cloning and characterisation of two DNA sequences shown in SEQ ID NO 1 and 2, respectively, which both:

1) have yeast promoter activity, and
2) have improved properties for expression cloning in yeast.

Further deletion studies on both yeast promoter sequences have identified the most important regions for each yeast promoter.

For the yeast promoter shown in SEQ ID NO 1, the most important region is from position −241 to −41 and for the yeast promoter shown in SEQ ID NO 2, it is from position −163 to −3. For further details see example 8.

Accordingly, in a first aspect the invention relates to a cloned yeast promoter DNA sequence, which comprises
a) the DNA sequence from position −241 to −41 shown in SEQ ID NO 1, or
b) an analogue of the DNA sequence defined in a) which
  i) is at least 90% homologous with said DNA sequence, or
  ii) hybridises with the same nucleotide probe as the DNA sequence defined in a).

In a second aspect the invention relates to a cloned yeast promoter DNA sequence, which comprises
a) the DNA sequence from −163 to −3 shown SEQ ID NO 2, or
b) an analogue of the DNA sequence defined in a) which
  i) is at least 90% homologous with said DNA sequence, or
  ii) hybridises with the same nucleotide probe as DNA sequence defined in a).

In a further aspect the invention relates to an expression vector comprising a cloned yeast promoter according to the invention.

In a further aspect the invention relates to the use of said expression vector for expression cloning in yeast.

Further the invention relates to a process for producing a polypeptide of interest in a yeast host cell, the process comprising transforming a suitable yeast host cell with a recombinant expression vector comprising i) a yeast promotor of the invention and ii) a DNA sequence coding for a polypeptide of interest, culturing the transformed cells under suitable conditions to express the polypeptide, and recovering the expressed polypeptide from the culture.

Finally the invention relates to the use of a polypeptide produced as described above for various industrial applications.

BRIEF DESCRIPTIONS OF DRAWINGS

Figure 1B:
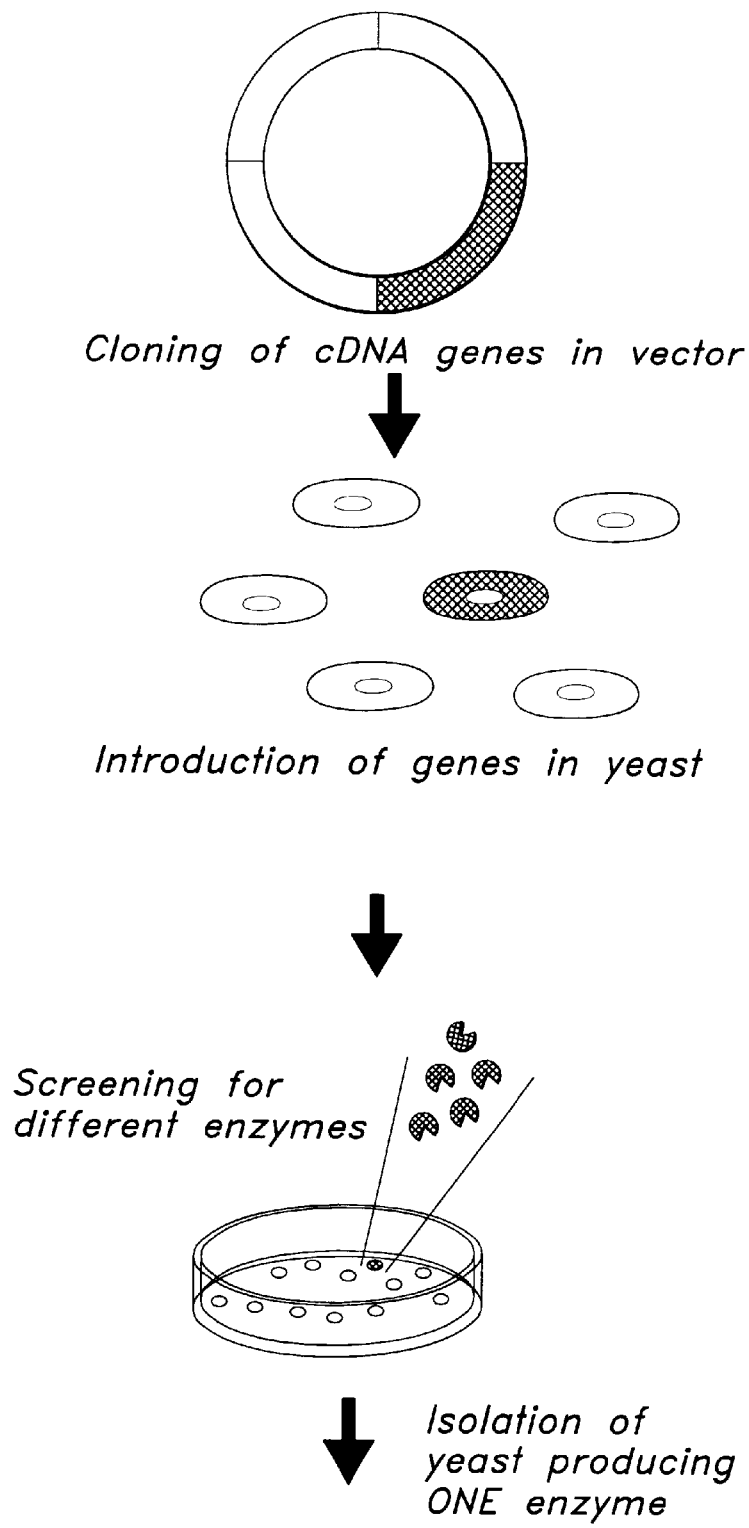
Figure 1C:
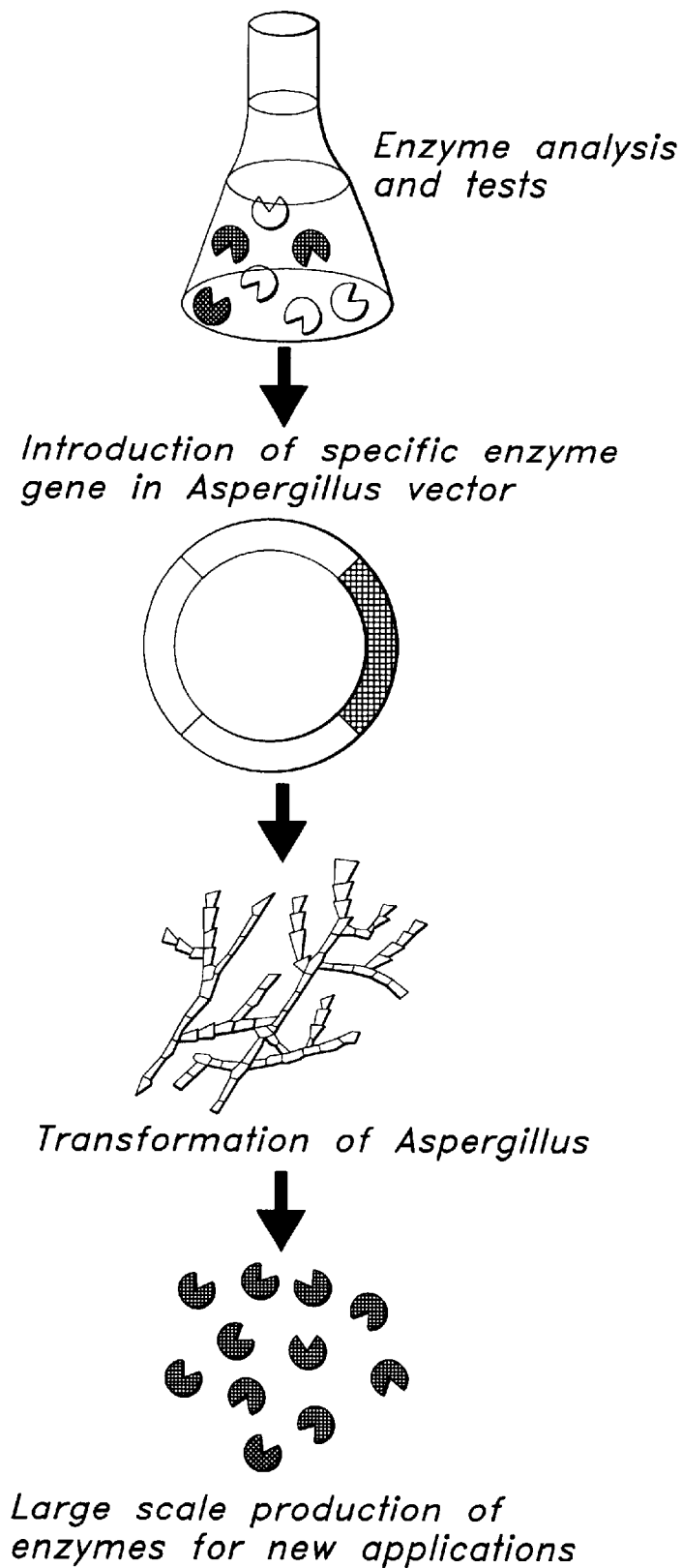

FIG. 1: Flow scheme of expression cloning.

Figure 2A:
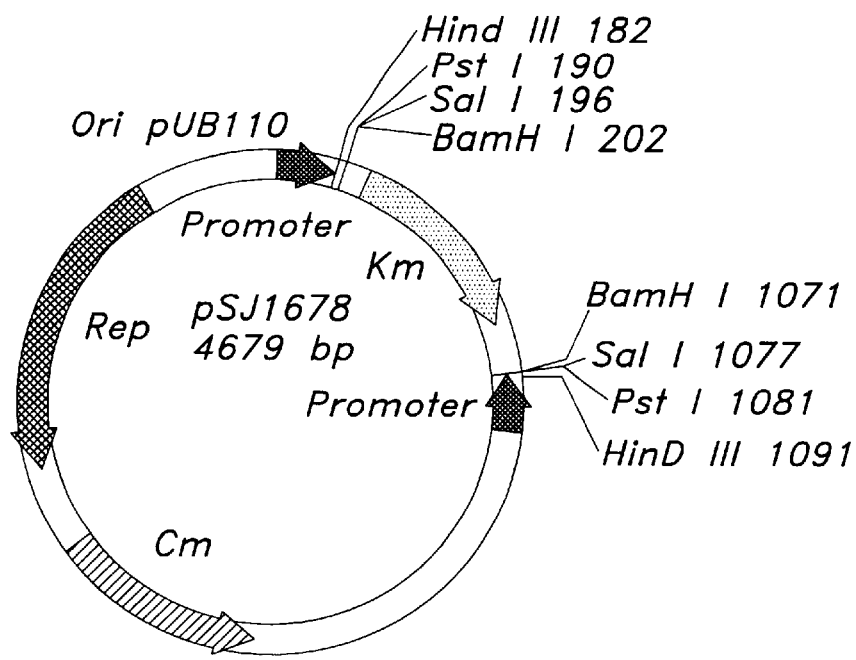
Figure 2B:
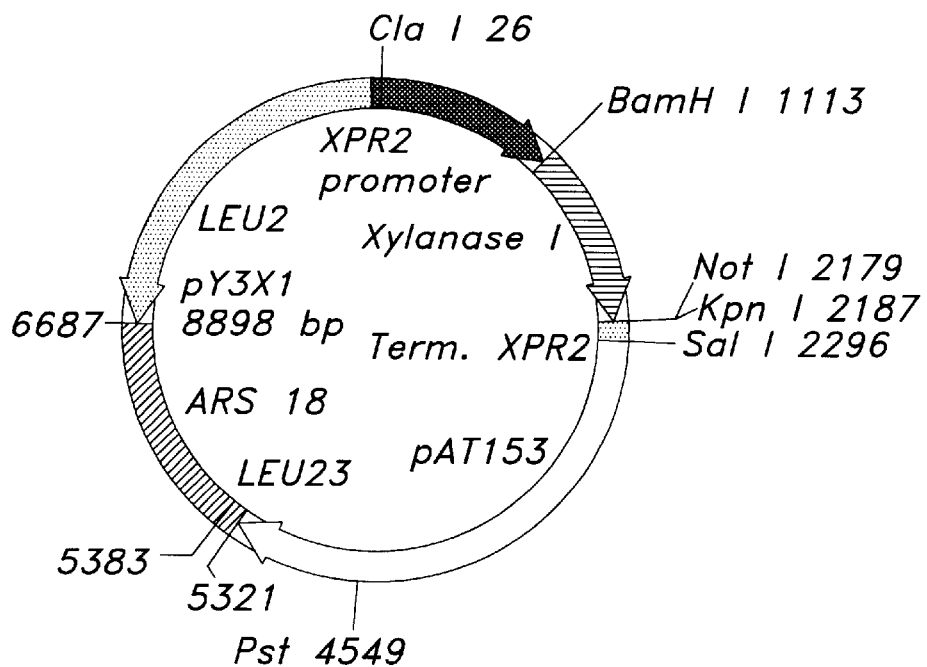

FIGS. 2A and 2B: Plasmid used for construction of the genomic library (A). The SauA I digested genomic DNA was cloned at the BamHI sites after removal of the kanamycine resistance gene. The kanamycine resistance gene is flanked by two inverted repeats which spoils the ability of the plasmid to replicate unless separated by an insert.

(B) Example of an expression vector used for examination of the different yeast promoter sequences. All expression vectors used contain selection markers and sequences for replication in *E. coli* and *Y. lipolytica* as in pY3X1 (see FIG. 2). The different yeast promoter sequences were cloned as ClaI/BamHI fragments and tested in constructs in which either the 43 kD Cellulase II (WO 91/17243) or Xylanase I from *Humicola insolens* (WO 92/17573) were used as reporter genes.

Figure 3:
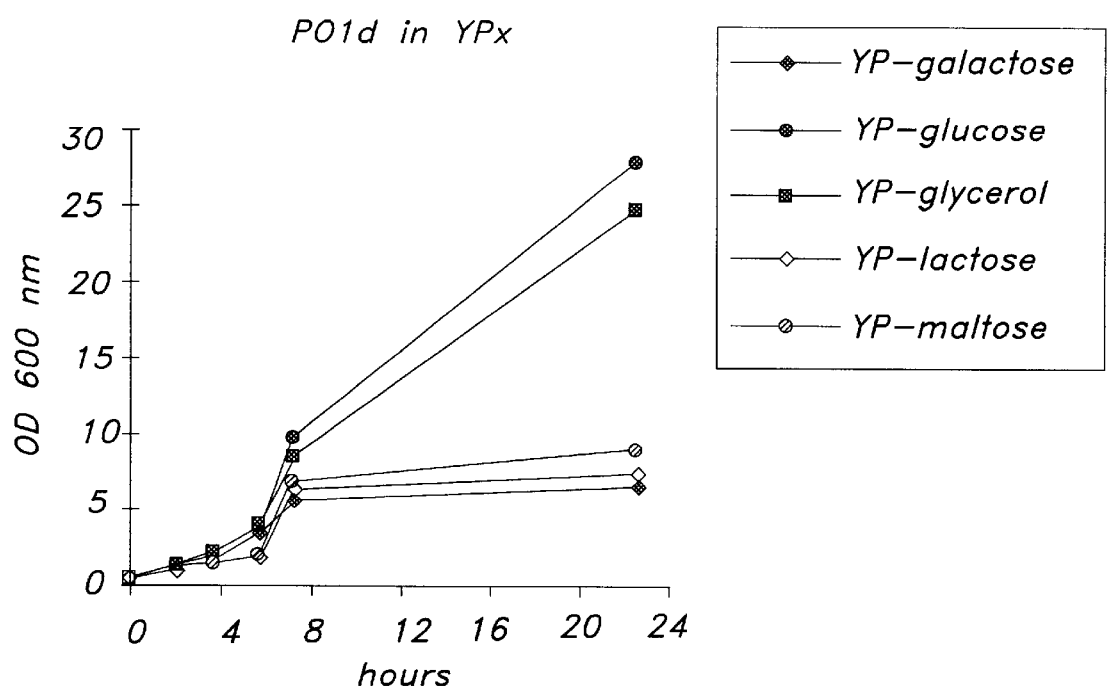

FIG. 3. Yeast strain PO1d grown in YP medium added 2% galactose, glucose, glycerol, lactose or maltose. Used to identify optimal conditions for making an PO1d cDNA library (see example 1).

FIG. 4. Frequency of cDNA sequences selected for further examination. L1 and L2 refer to the library from which the sequences come and the subsequent number refers to the clone number in the library concerned. Variation in starting point of the sequences reflects the cDNA synthesis events. The sequences that include the most of the 5' end of the sequences were used for further analysis. (see example 2–7).

Figure 5:
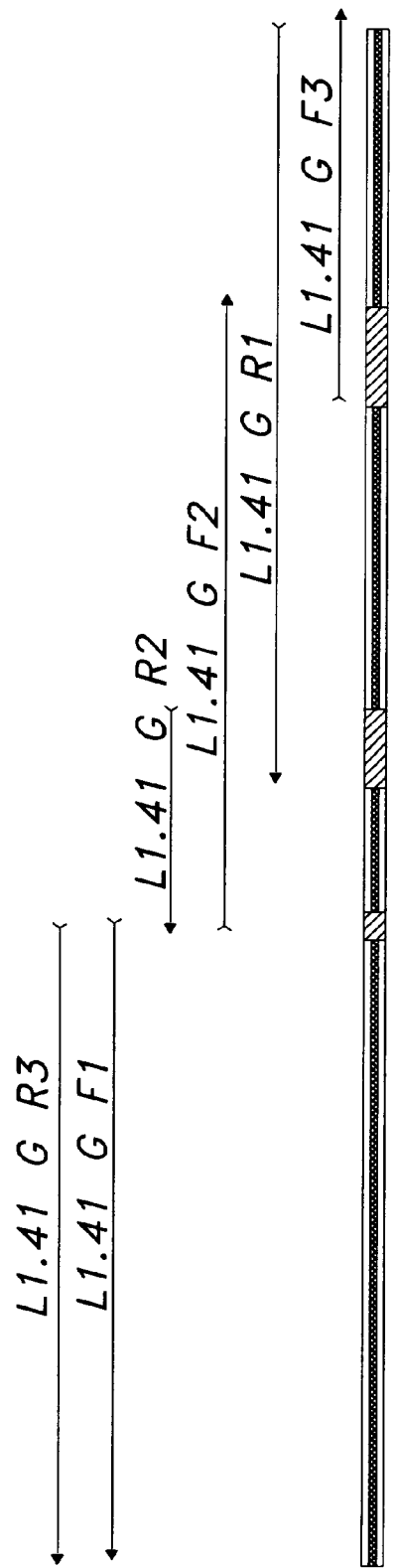

FIG. 5. Strategy used for sequence determination of the L1.41 related genomic DNA.

FIG. 6. Nucleotide sequence of the relevant part of the L1.41 related genomic DNA (L1.41 is identical to SEQ ID NO 1). The positions are related to the A in the ATG start codon (bold), defined as +1. The putative UAS*boxes HOMOL1 (position ÷191–÷180) and RPG (÷179–÷168) and the T-rich sequence are underlined. The putative TATA box (÷111–÷106) and a pyrimidine-rich sequence (÷85–÷58) are double underlined. The putative transcription initiation site (÷56–÷53) is written in bold. Nucleotides located from position ÷40 and downstream were also present in the cDNA sequence.

FIG. 7. The nucleotide sequence and the deduced amino acid sequence of the translation elongation factor EF-1 cDNA from *Y. lipolytica*. Restriction sites for HindIII (position 224) and KpnI (position 353). This sequence is identical to SEQ ID No 3.

FIG. 8. Nucleotide sequence of the L2.17 related genomic DNA (L2.17 is identical to SEQ ID NO 2). The positions are related to the A in the ATG start codon defined as +1. The putative UAS*boxes HOMOL1 (position ÷273–÷262) and RPG (÷247–÷236) and the T-rich sequence (present on the opposite strand) are double underlined Putative TATA boxes (÷201–÷190), a TATA-like sequence (÷46–÷41) and transcription initiation consensus sequences (÷8, ÷55, ÷15 and ÷13) are underlined. The genomic sequence (including the ATG start codon) also present in the cDNA sequence (165–173) and the 3' splice site (176–178) of the intron are written in bold.

FIG. 9. The nucleotide sequence and the deduced amino acid sequence of Ribosomal protein S7 cDNA from *Y. lipolytica*. The KpnI restriction site (position 445) is underlined. This sequence is identical to SEQ ID No 4.

FIGS. 10A–D. The strategy used for deletion analysis of the TEF gene yeast promoter sequence (seq. ID. No. 1). The part of genomic sequence located upstream the cDNA sequence. (B, C, D) 5' deletions of th sequence in (A). As shown, neither of the deletions affected the putative elements of the basal yeast promoter region. In edition D, the putative UAS* boxes are deleted.

FIGS. 11A–G. The strategy planned for deletion analysis of the ribosomal protein S7 yeast promoter sequence (seq. ID No. 2). Successful cloning was only obtained for B, D and F. In D, the putative TATA-box and the putative UAS*boxes are excluded. In F the TATA-like sequence and the four 3' terminal transcription initiation consensus sequences are excluded.

FIGS. 12A–D. Initial activity measurement of the yeast promoters of the invention (A and B).SC÷leu growth plate+ AZCL Birch xylan substrate (B). PO1d XPR2 optimal medium growth plates+AXCL HE-cellulose substrate (C).XPR2 optimal medium growth plates+AZCL Birch xylan substrate (D). The vector constructions are described in Table 1.

DETAILED DESCRIPTION OF THE INVENTION

Cloned yeast promoters

In preferred embodiments the present invention provides two cloned yeast promoters. One of the promoters comprises
a) the DNA sequence from position −241 to −41 shown in SEQ ID NO 1 , or
b) an analogue of the DNA sequence defined in a) which
  i) is at least 90% homologous with said DNA sequence, or
  ii) hybridises with the DNA sequence defined in a).

The other promoter comprises
a) the DNA sequence from −163 to −3 shown SEQ ID NO 2, or
b) an analogue of the DNA sequence defined in a) which
  i) is at least 90% homologous with said DNA sequence, or
  ii) hybridises with the DNA sequence defined in a).

The promoters of the invention may comprise additional nucleotides to those specified above. In particular the promoter may comprise nucleotides −407 to −41 of SEQ ID NO 1 or nucleotides −543 to −3 of SEQ ID NO 2.

A cloned yeast promoter, refers to a yeast promoter cloned by standard cloning procedure used in genetic engineering to relocate a segment of DNA from its natural location to a different site where it will be reproduced. The cloning process involves excision and isolation of the desired DNA segment, insertion of the piece of DNA into the vector molecule and incorporation of the recombinant vector into a cell where multiple copies or clones of the DNA segment will be replicated.

As defined herein, a DNA sequence analogous to either of the two isolated DNA sequence of the present invention is intended to indicate any yeast promoter DNA sequence, which DNA sequence has one or more of the properties cited under (i)–(ii) above.

The yeast promoter DNA sequence of the invention may be isolated from a *Yarrowia lipolytica* yeast strain, or another or related organism, as will be described in further detail further below (see section "Microbial sources").

Alternatively, the promoter sequence of the invention may be constructed on the basis of the DNA sequence presented as DNA sequence shown in SEQ ID NO 1 or SEQ ID NO 2, e.g. be a subsequence thereof, or a DNA sequence resulting from introduction of one or more nucleotide substitutions (i.e. deletions, insertions, substitutions, or addition of one or more nucleotides in the sequence) which do not effect (in particular impair) the yeast promoter activity.

Regions which can be modified without significantly effecting the yeast promoter activity can be identified by deletion studies. For further details see example 8.

The homology referred to in i) above is determined as the degree of identity between the two sequences indicating a derivation of the first sequence from the second. The homology may suitably be determined by means of computer programs known in the art such as GAP provided in the GCG program package (Needleman, S. B. and Wunsch, C. D., (1970), Journal of Molecular Biology, 48, 443–453). Using GAP with the following settings for DNA sequence comparison: GAP creation penalty of 5.0 and GAP extension penalty of 0.3, the coding region of the DNA sequence exhibits a degree of identity preferably of at least 90%, more preferably at least more preferably at least 95%, more preferably at least 97% with any of the DNA sequence shown in SEQ ID No. 1 or 2.

The hybridisation referred to in (ii) above is intended to indicate that the analogous DNA sequence hybridises to the yeast promoter DNA sequence under certain specified conditions which are described in detail in the Materials and Methods section hereinafter. The oligonucleotide probe to be used is the DNA sequence from position −241 to −41 in SEQ ID NO 1 or from −163 to −3 in SEQ ID NO 2. The oligonucleotide probe used herein is preferably a double-stranded DNA probe.

The DNA sequence encoding a yeast promoter of the invention can be isolated from a suitable organism by colony hybridisation using a 5'-cDNA sequence from the corresponding coding sequence.

An example of a flowscheme for such a cloning strategy is given just below and for further details see example 1–7.

Construct a yeast promoter containing cDNA libraries, e.g. a *Y. lipolytica* cDNA library Determine sequences of 100 arbitrarily chosen clones from each library—examine for repeats Identify the yeast promoter sequences of highly expressed genes by hybridization to a genomic library Clone the yeast promoters in reporter constructs and characterize the yeast promoter.

Alternatively, the DNA encoding a yeast promoter of the invention may, in accordance with well-known procedures, conveniently be isolated from a suitable source, such as any of the below mentioned organisms, by use of synthetic oligonucleotide probes prepared on the basis a DNA sequence disclosed herein. For instance, a suitable oligonucleotide probe may be prepared on the basis of nucleotide sequences presented as SEQ ID No. 1 or 2.

Expression cloning

In the present context the term "expression cloning in yeast" refers to the technique described by Dalbøge and Heldt-Hansen (A novel method for efficient expression cloning of fungal enzyme genes. Mol. Gen. Genet. 243: 253–260. (1994), WO 93/11249).

The principle in the expression cloning technique is further outlined in FIG. 1.

Briefly the principle of the technique is following. When an organism that secretes an enzyme of interest is identified, it is grown at inducing conditions and poly(A) enriched RNA is isolated. A directional cDNA library is constructed in a *E. coli*/yeast shuttle vector under control of a yeast promoter and *E. coli* is transformed. Plasmid DNA is isolated and introduced into a yeast strain, e.g. *S. cerevisiae*. The yeast cells are spread on selective growth plates and replicated to selective and inducing plates which contain the relevant enzyme substrate, e.g. xylan when screening for xylanase activity. The xylan is e.g. added as cross linked insoluble granules, which in the presence of xylanase activity will be degraded, leading to a dyed halo formation around the positive yeast colonies.

When a positive yeast colony has been identified and retested, the cDNA is isolated and cloned in an *A. oryzae* expression vector. *A. oryzae* is transformed which makes large scale production of the enzyme possible (Christensen et al, 1988).

Yeast promoter:

Yeast promoter refers to the nucleotide sequence(s) at the 5' end of a structural gene which direct(s) the initiation of transcription. The promoter sequence is to drive the expression of a downstream gene. The promoter drives transcription by providing binding sites to RNA polymerases and other initiation and activation factors. Usually the promoter drives transcription preferentially in the downstream direction. The level of transcription is regulated by the promoter. Thus, in the construction of heterologous promoter/structural gene combinations, the structural gene is placed under the regulatory control of a promoter such that the expression of the gene is controlled by the promoter sequence(s). The promoter is positioned preferentially upstream to the structural gene and at a distance from the transcription start site that approximates the distance between the promoter and the gene it controls in its natural setting. As it is known in the art, some variation in this distance can be tolerated without loss of promoter function.

The transcription efficiency of the promoter may, for instance, be determined by a direct measurement of the amount of mRNA transcription from the promoter, e.g. by Northern blotting or primer extension, or indirectly by measuring the amount of gene product expressed from the promoter.

A FastA search (Pearson and Lipman. P.N.A.S. USA 85: 2444–2448 (1988)) on the GenEMBL database showed significant similarity of the downstream cDNA sequence, controlled by the yeast promoter shown in SEQ ID NO 1, to the translation elongation factor EF-1a gene (TEF) of various sources, e.g. *Arxula adeninivorans, Neurospora crassa* and *Saccharomyces cerevisiae*.

In the present context the term "EF-1a yeast promoter" is used to indicate the upstream untranslated region upstream of the ATG start codon for the EF-1 a gene (e.g. ATG start codon in SEQ ID NO 3) which contain most, if not all, features required for expression. For further details see Example 6.

A similar FastA search on cDNA sequence, controlled by the yeast promoter shown in SEQ ID NO 2 showed significant similarity to the ribosomal protein S7 (RP s7) of *S. cerevisiae* and the corresponding ribosomal protein S4 of e.g. *D. melanogaster* and *H. sapiens*.

In the present context the term "ribosomal protein S7 yeast promoter" is used to indicate the upstream untranslated region upstream of the ATG start codon for the ribosomal protein S7 gene (e.g. ATG start codon in SEQ ID NO 4) which contain most, if not all, features required for expression. For further details see Example 7.

Both the EF-1a and ribosomal protein S7 are essential for growth of *Y. lipolytica*. Thus the pH tolerance of both the EF-1a yeast promoter and ribosomal protein S7 yeast promoter is as least the pH range where *Y. lipolytica* is able to growth.

For both yeast promoters of the invention this is estimated to be in the pH range preferably from 4–11, more preferably from 4–10, more preferably from 4–9, more preferably from 4–8, more preferably from 5–11, more preferably from 5–10, more preferably from 5–9, more preferably from 5–8.

In the context of expression cloning an ideal yeast promoter meet the following criteria:

Strength. A strong yeast promoter is a necessary premise for a high expression level, and the low copy number of the ars18 Fournier, P. et al. Yeast 7:25–36 (1991)) based expression vectors makes this demand even more important when *Y. lipolytica* is used as the host organism.

Activity in a suitable medium. In the context of expression cloning a suitable medium is a medium from which it is easy to purify the secreted product for initial characterisation and it is a medium which is selective.

Use of a selective medium makes it possible to screen directly for positive clones.

pH tolerance. If the enzymes of interest are known to be active only in e.g. an acidic environment, direct screening will only be possible on corresponding plates. pH tolerance is of course limited by the tolerance of the host organism. Inducibility. A tightly regulated yeast promoter makes it possible to separate the growth stage from the expression stage, thereby enabling expression of products which are known to inhibit cell growth.

The *Yarrowia lipolytica* XPR2 yeast promoter of the prior art:

The XPR2 gene from *Y. lipolytica* encodes an inducible alkaline extracelluar protease (AEP) which is the major protein secreted by this yeast (Davidow et al, 1987 b). Induction of AEP occurs at pH above 6.0 on media lacking preferred carbon and nitrogen sources and full induction requires high levels of peptones in the culture medium (Ogrydziak et al, 1977; Ogrydziak and Scharf, 1982). The regulation of the XPR2 gene is very complex and not yet fully understood.

The fact that the XPR2 yeast promoter is only active at pH above 6.0 on media lacking preferred carbon and nitrogen sources and full induction requires high levels of peptone in the culture medium is highly disadvantageous for the use of such yeast promoter in expression cloning in yeast. The demand for pH above 6.0 in the medium makes it impossible to screen directly for secreted enzymes that are active only in an acidic environment. The presence of peptone in the medium complicates product recovery and purification. Finally the presence of peptone hinders the direct screening for transformants based on LEU2 selection.

In contrast to the known XPR2 yeast promoter of *Y. lipolytica* the yeast promoters of the present invention is active preferably in the pH range from 4 to 11 (see above), and do not require peptone in the medium or any other ingredients, which seriously complicates product recovery and purification. Therefore the yeast promoter of the invention is highly suitable for use in expression cloning in yeast and recombinant expression in general.

A comparative study of the XPR2 yeast promoter and the yeast promoters of the invention is provided in Example 9. In example 9 it is shown that the yeast promoters of the invention is improved compared to the XPR2 yeast promoter, when tested for yeast promoter activity on growth plates, which can be considered as an imitation of a screening event.

Microbial Sources

In a preferred embodiment, a yeast promoter of the invention is derived from a Yarrowia lipolytica yeast strain.

It is at present contemplated that a yeast promoter of the invention, i.e. an analogous yeast promoter, may be obtained from other micro-organisms. For instance, the yeast promoter may be derived from other yeast strains, such as a strain of *Saccharomyces cerevisiae.*

Expression vector

In another aspect, the invention provides a recombinant expression vector comprising a yeast promoter of the invention.

The expression vector of the invention may be any expression vector that is conveniently subjected to recombinant DNA procedures, and the choice of vector will often depend on the host cell into which it is to be introduced.

The expression vector may e.g. be used for achieving expression cloning in yeast or for the production of heterologous polypeptide of interest. In the latter case, the expression vector comprises i) a yeast promoter of the invention and ii) a DNA sequence coding for a polypeptide of interest.

In a expression vector for use in expression cloning in yeast, cDNA's to be screened according to the expression cloning technique described in WO 93/11249 should be operable connected to a yeast promoter of the present invention and a terminator sequence (see WO 93/11249).

Further the expression vector may be used to enable recombinant production of a heterologous and/or homologous protein of interest, preferably an enzyme of interest.

The procedures used to ligate the DNA sequences coding for the cDNA library, a DNA sequence coding for a protein of interest, the yeast promoter and the terminator, respectively, and to insert them into suitable vectors are well known to persons skilled in the art (cf., for instance, Sambrook et al., (1989), Molecular Cloning. A Laboratory Manual, Cold Spring Harbor, N.Y.).

Yeast host cells

In yet another aspect the invention provides a host cell comprising the recombinant expression vector of the invention.

Preferably, the host cell of the invention is a eucaryotic cell, in particular a yeast cell.

Examples of such yeast host cell include, but are not limited to a strain of Saccharomyces, in particular *Saccharomyces cerevisae, Saccharomyces kluyveri* or *Saccharomyces uvarum*, strain of Schizosaccharomyces sp., such as *Schizosaccharomyces pombe*, a strain of Hansenula sp., Pichia sp., Yarrowia sp., such as *Yarrowia lipolytica*, or Kluyveromyces sp., such as *Kluyveromyces lactis.*

Especially a strain of *Yarrowia lipolytica* is a suitable host for the present invention.

Process of producing a polypeptide

In a still further aspect, the present invention provides a process of producing polypeptide of interest, wherein a suitable host cell, which has been transformed with a expression vector comprising i) the yeast promoter of the invention and ii) a DNA sequence coding for a polypeptide of interest, is cultured under conditions permitting the production of the polypeptide, and the resulting polypeptide is recovered from the culture.

The polypeptide may be a protein, e.g. an enzyme such as a protease, amylase or lipase.

The medium used to culture the transformed host cells may be any conventional medium suitable for growing the host cells in question. The expressed polypeptide of interest may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The invention is described in further detail in the following examples which are not in any way intended to limit the scope of the invention as claimed.

MATERIALS AND METHODS

General methods

If not further specified, all the experimental techniques referred to below were performed by standard techniques within the field of recombinant DNA technology, cf. Sambrook et al., 1989.

All experimental techniques include among others construction of plasmids, ligation, transformation, sequencing, hybridization, and etc.

Restriction endonucleases were purchased from New England Biolabs and Boehringer Mannheim and used as recommended by the manufacturers. T4 DNA ligase was purchased from New England Biolabs and used as recommended by the manufacturer.

Strains, plasmids, and transformation procedures

Bacterial strains used were *Escherichia coli* MC1061 (Wertman, K. F. et al 1986); SJ2, a derivative of C600 (Raleigh, E. A. et al 1988); and DH10BÔ (Gibco BRL). The *Yarrowia lipolytica* strain used was P01d (W29 derivative) ura 3-302, leu 2-270, xpr 2-322 a (gift from Claude Gaillardin, Centre de Biotechnologie Agro-Industrielle, France.)

Plasmids used are described in table I and FIG. 2. Those carrying deletions in the cloned yeast promoters are described in FIGS. 10 and 11. All deletions were introduced into pY5TA- 43 kD/X1 or pY5RB- 43 kD/X1.

*Y. lipolytica* was transformed by electrotransformation. SJ2 and DH10B were transformed by electrotransformation and MC1061 by ordinary transformation.

Enzymes used as reporter genes:

43 kD Cellulase II from *Humicola insolens* described in WO 91/17243.

Xylanase I from *Humicola insolens* described in WO 92/17573.

TABLE I. Plasmids used (except those carrying yeast promoter deletions).

| Plasmid | Use/relevant features | Source |
| --- | --- | --- |
| pSJ1678 | Bacillus/*E. coli* shuttle vector used for cloning of Sau 3A I digested P01d genomic DNA (FIG. 2). | |
| PUC19 | Used for sequence determination of positives from P01d genomic library originally cloned in pSJ1678. | Yanisch-Perron, C. et al 1985 |
| pYES 2.0 | Used for cloning of P01d cDNA libraries as BstXI/NotI fragments. | Invitrogen USA |
| pY343kD | *Y. lipolytica* expression vector based on the XPR2 yeast promoter and the LEU2 gene as a selection marker. The 43kD cellulase II from *Humicola insolens* is used as a reporter gene. pY343kD is similar to pY3X1 (FIG. 2), where in pY343kD cellulase II is used as reporter gene in stead of Xylanase I. | |
| PY3X1 | *Y. lipolytica* expression vector based on the XPR2 yeast promoter and the LEU2 gene as a selection marker. The xylanase I from *Humicola insolens* is used as a reporter gene, (see FIG. 2). | |
| PY5TA43kd | Based on pY343kD. The XPR2 yeast promoter sequence has been removed as a ClaI/BamHI fragment and replaced by the translational elongation factor 1a yeast promoter sequence edition A cloned in this study, (see FIG. 10). | |
| PY5TAX1 | Based on pY3X1. The XPR2 yeast promoter sequence has been removed as a ClaI/BamHI fragment and replaced by the translational elongation factor 1a yeast promoter sequence edition A cloned in this study, (see FIG. 10) | |
| PY5RB43kd | As pY5TA43kD, except that the ribosomal protein S7 yeast promoter sequence edition B cloned in this study is used as the yeast promoter, (see FIG. 11). | |
| PY5RBX1 | As pY5TAX1, except that the ribosomal protein S7 yeast promoter sequence edition B cloned in this study is used as the yeast promoter, (see FIG. 11). | |
| PY543kDCV | Control vector based on pY343kD. The XPR2 yeast promoter sequence has been removed as a ClaI/BamHI fragment and the vector religated after blunt ending by Mung Bean Nuclease treatment. | |
| PY5X1CV | Control vector based on pY3X1. The XPR2 yeast promoter sequence has been removed as a ClaI/BamHI fragment and the vector religated after blunt ending by Mung Bean Nuclease treatment. | |

Further details of strains:

*E. coli* strains
 For use in the vector construction work:
MC1061
F$^-$ araD139 D(ara-leu)7696 galE15 galK16 D(lac)X74 rpsL (Str$^r$) hsdR2 ($r_k^-$ $m_k^+$) mcrA mcrB1
As host strain for *Yarrowia lipolytica* P01d cDNA libraries:
DH10B(Gibco BRL)
F mcrA D(mrr-hsdRMS-mcrBC) F80dlacZDM15 DlacX74 deoR recA1 endA1 araD139 D(ara, leu)7697 galU gal K 1$^-$ rpsL nupG
As host strain for *Yarrowia lipolytica* P01d genomic library:
SJ2: A C600 derivate (Raleigh et al, 1988).
For site-specific mutagenesis on pY1:
*E. coli* BMH71-18 mut S. thi sup E Δ(lac-pro AB) [mutS::Tn10] F' [proAB$^+$ lacI$^q$ lac Z ΔM15]
Yeast strains
*Yarrowia lipolytica*
P01d: ura 3-302 leu 2-270 xpr 2-322
E129: Mat A lys 11-23 ura 3-302 leu 2-270 xpr 2-322
E150: Mat B his-1 ura 3-302 leu 2-270 xpr 2-322
ura 3-302 is a disruption of URA3
leu 2-270 is an internal deletion
xpr 2-322 is a deletion removing transcriptional start, ATG, and part of the pre-pro region.
*Saccharomyces cerevisiae* JG169:
W 3124:
Mat a ura 3-52 leu 2 - 3,112 his 3-D200 pep4-1137 D prc1::HIS3 prb1::LEU 2 cir$^+$
*Hansenula polymorpha* A16:
Transformant are selected on the basis of a defective Leucine gene.
*Schizosaccharomyces pombe* 972: h ura4-294
*Kluyveromyces lactis* MW98-8C: Mat a uraA arg lys K$^+$ pKD1$^0$
Transformation of yeast cells:
Electro-competent yeast cells
 This *S. cerevisiae* protocol was used without modifications to make electro-competent *Yarrovia lipolytica* P01d cells.
1. Inoculate 500 ml YPD with an aliquot from an overnight culture. Grow with vigorous shaking at 30° C. to an OD$_{600}$ of 1.3–1.5 (approximately 1×10$^8$ cells/ml.
2. Divide the culture into two centrifuge bottles and spin at 5000 rpm for 5' at 4° C. in a Beckman centrifuge. Discard the supernatant.
3. Resuspend in a total of 500 ml ice-cold sterile water and centrifuge as above. Discard the supernatant.
4. Resuspend in a total of 250 ml. Pool the two 125 ml aliquots into a single bottle and centrifuge as above. Discard the supernatant.
5. Resuspend in 20 ml ice-cold 1 M sorbitol. Transfer to a chilled 30 ml centrifuge tube. Centrifuge as above and discard the supernatant.
6. Resuspend by adding 0.5 ml ice-cold 1 M sorbitol. Store on ice.
 The cells can be stored at ÷80° C. for several month. It is very important to keep the culture and all solutions cold durring the treatment of the cells.

Culture media and growth conditions.

Prior to the construction of cDNA libraries, initial growth experiments with P01d were performed in YP medium, with addition of 2% of the various carbohydrate sources tested. Cells were grown at 30° C. MC1061 and DH10B transformants were grown in LB medium+100 mg/ml ampicillin. SJ2, transformed with pSJ1678, in which P01d genomic DNA was cloned as Sau 3A I fragments, was grown in LB+10 mg/ml chloramphenicol. For Northern blot analysis and contruction of cDNA libraries, P01d cultures were grown in YP+2% glucose or 2% glycerol (library 1 and 2 respectively) at 30° C. and cells were harvested late in the logarithmic phase at a optical density of 600 nm ($OD_{600}$) of 5.5. For construction of a genomic library and Southern blot analysis P01d cultures were grown in YP-glucose. For cellulase and xylanase assays, positives were precultured in SC,leu medium and the respective inducing growth media inoculated to an $OD_{600}$ of 0.1. Transformants containing XPR2 yeast promoter based vectors were grown in XPR2 optimal medium. SC,leu medium was used as inducing medium for transformants in which the novel yeast promoter sequences were introduced. Transformants were grown in 100 ml media in 500 ml bottles at 30° C., 250 rpm. Samples were taken 3 times during the logarithmic phase (SC,leu cultures $OD_{600}$<0.5, XPR2 optimal medium cultures $OD_{600}$<10 and 3 times during the stationary phase.

Extraction of total RNA is performed with guanidinium thiocyanate followed by ultracentrifugation through a 5.7 M CsCl cushion, and isolation of poly(A)$^+$RNA is carried out by oligo(dT)-cellulose affinity chromatography using the procedures described in WO 94/14953.

cDNA synthesis: Double-stranded cDNA is synthesized from 5 mg poly(A)$^+$ RNA by the RNase H method (Gubler and Hoffman (1983) Gene 25:263–269, Sambrook et al. (1989) Molecular cloning: A laboratory manual, Cold Spring Harbor lab., Cold Spring Harbor, N.Y.) using the hair-pin modification developed by F. S. Hagen (pers. comm.). The poly(A)$^+$ RNA (5 mg in 5 ml of DEPC-treated water) is heated at 70° C. for 8 min. in a pre-siliconized, RNase-free Eppendorph tube, quenched on ice and combined in a final volume of 50 ml with reverse transcriptase buffer (50 mM Tris-Cl, pH 8.3, 75 mM KCl, 3 mM $MgCl_2$, 10 mM DTT, Bethesda Research Laboratories) containing 1 mM of dATP, dGTP and dTTP and 0.5 mM 5-methyl-dCTP (Pharmacia), 40 units human placental ribonuclease inhibitor (RNasin, Promega), 1.45 mg of oligo(dT)$_{18}$-Not I primer (Pharmacia) and 1000 units SuperScript II RNase H reverse transcriptase (Bethesda Research Laboratories). First-strand cDNA is synthesized by incubating the reaction mixture at 45° C. for 1 hour. After synthesis, the mRNA:cDNA hybrid mixture is gelfiltrated through a MicroSpin S-400 HR (Pharmacia) spin column according to the manufacturer's instructions.

After the gelfiltration, the hybrids are diluted in 250 ml second strand buffer (20 mM Tris-Cl, pH 7.4, 90 mM KCl, 4.6 mM $MgCl_2$, 10 mM $(NH_4)_2SO_4$, 0.16 mM bNAD+) containing 200 mM of each dNTP, 60 units *E. coli* DNA polymerase I (Pharmacia), 5.25 units RNase H (Promega) and 15 units *E. coli* DNA ligase (Boehringer Mannheim). Second strand cDNA synthesis is performed by incubating the reaction tube at 16° C. for 2 hours and additional 15 min. at 25° C. The reaction is stopped by addition of EDTA to a final concentration of 20 mM followed by phenol and chloroform extractions.

Mung bean nuclease treatment: The double-stranded cDNA is precipitated at –20° C. for 12 hours by addition of 2 vols 96% EtOH, 0.2 vol 10 M $NH_4Ac$, recovered by centrifugation, washed in 70% EtOH, dried and resuspended in 30 ml Mung bean nuclease buffer (30 mM NaAc, pH 4.6, 300 mM NaCl, 1 mM $ZnSO_4$, 0.35 mM DTT, 2% glycerol) containing 25 units Mung bean nuclease (Pharmacia). The single-stranded hair-pin DNA is clipped by incubating the reaction at 30° C. for 30 min., followed by addition of 70 ml 10 mM Tris-Cl, pH 7.5, 1 mM EDTA, phenol extraction and precipitation with 2 vols of 96% EtOH and 0.1 vol 3 M NaAc, pH 5.2 on ice for 30 min.

Blunt-ending with T4 DNA polymerase: The double-stranded cDNAs are recovered by centrifugation and blunt-ended in 30 ml T4 DNA polymerase buffer (20 mM Tris-acetate, pH 7.9, 10 mM MgAc, 50 mM KAc, 1 mM DTT) containing 0.5 mM of each dNTP and 5 units T4 DNA polymerase (New England Biolabs) by incubating the reaction mixture at 16° C. for 1 hour. The reaction is stopped by addition of EDTA to a final concentration of 20 mM, followed by phenol and chloroform extractions, and precipitation for 12 hours at –20° C. by adding 2 vols 96% EtOH and 0.1 vol 3 M NaAc pH 5.2.

Adaptor ligation, Not I digestion and size selection: After the fill-in reaction the cDNAs are recovered by centrifugation, washed in 70% EtOH and dried. The cDNA pellet is resuspended in 25 ml ligation buffer (30 mM Tris-Cl, pH 7.8, 10 mM $MgCl_2$, 10 mM DTT, 0.5 mM ATP) containing 2.5 mg non-palindromic BstXI adaptors (Invitrogen) and 30 units T4 ligase (Promega) and incubated at 16° C. for 12 hours. The reaction is stopped by heating at 65° C. for 20 min. and then cooling on ice for 5 min. The adapted cDNA is digested with Not I restriction enzyme by addition of 20 ml water, 5 ml 10× Not I restriction enzyme buffer (New England Biolabs) and 50 units Not I (New England Biolabs), followed by incubation for 2.5 hours at 37° C. The reaction is stopped by heating at 65° C. for 10 min. The cDNAs are size-fractionated by gel electrophoresis on a 0.8% SeaPlaque GTG low melting temperature agarose gel (FMC) in 1× TBE to separate unligated adaptors and small cDNAs. The cDNA is size-selected with a cut-off at 0.7 kb and rescued from the gel by use of β-Agarase (New England Biolabs) according to the manufacturer's instructions and precipitated for 12 hours at –20° C. by adding 2 vols 96% EtOH and 0.1 vol 3 M NaAc pH 5.2.

Construction of directional cDNA libraries

Total RNA was extracted and poly(A)+RNA isolated. From 500 ml cultures (>>$2.75 \times 10^{10}$ cells) a yield of 1.9 mg and 2.9 mg total RNA was obtained (library 1 and 2 respectively). Isolation of poly(A)+RNA yielded 1.1% and 2.2% (library 1 and 2 respectively). Double stranded cDNA was synthesised from 5 mg poly(A)+RNA as described. The method includes introduction of a 3' NotI site by the oligo(dT)-NotI anchor primer. Size estimation of the double stranded cDNA on 1% agarose showed a distribution of the product between 0.3 Kb and 10 Kb. Removal of the single stranded hairpin DNA by Mung bean nuclease treatment and blunt ending with T4 DNA polymerase was followed by ligation of non-palindromic BstXI adaptors. After NotI digest a 5'BstXI 3'NotI product was obtained. The cDNA was size fractionated on a 0.8% low melt agarose gel and fragments >0.8 Kb were purified. Test ligations with different amounts of BstXI/NotI digested pYES 2.0 vectors, followed by electrotransformation of DH10B, did not result in saturation of the vector in any cases. Thus the sizes of the libraries were estimated to be at least $2 \times 10^6$ and $3 \times 10^5$ (library 1 and 2 respectively).

Sequence determination.

All sequence determinations were performed on ABI 373 or 377 DNA Sequencer and analysed by use of SequencerÔ 2.1 or 3.0 (Gene Codes Corporation, USA). Initial sequence determination of cDNA clones was performed only on one strand at the 5' end by use of a single primer. Selected cDNA clones were sequenced on both strands except at the sequence just upstream the poly A tail, were a single strand was sequenced twice with different primers. Sequence determination of positive clones from the genomic libraries was not possible when present in the pSJ1678 background, why these inserts were cloned in pUC19 prior to sequence determination of both strands. The genomic insert that responded to the L1.41 based probe was cloned in pUC19 as a SalI fragment, and the insert that responded to the L2.17 based probe was cloned as a PstI fragment, due to the presence of the remaining practicable cloning sites internal in these inserts.

Southern and Northern blots.

Southern blot analysis was carried out at standard conditions. For each analysis 4×10 mg P01d genomic DNA was digested to completion (20 unit enzyme, 3 hours incubation+ additional 10 unit enzyme and 2 hours incubation) and fractionated on 1% Sea Kem GTG agarose (FMC Bioproducts). To examine for DNase contamination 5 mg genomic DNA was incubated for 5 hours in one of the restriction buffers used for digestion. Polymerase chain reaction (PCR) copies of the respective cDNA's were used as probes. Radioactive labelling of the DNA by random priming was carried out.

Northern blot analysis was carried out at standard conditions. 2×2.5 mg poly(A)+RNA from library 1 and 2 was fractionated on 1% Sea Kem GTG agarose gels. One gel was used for ethidium bromide staining (60' in 0,1M $NH_4Ac$, 0.5 mg/ml EtBr) one gel was used for blotting. The same probes as in the Southern blot analysis were used. The membrane was exposed for 45' prior to development.

Preparation of total DNA from yeast:

The optimal method for preparation of total DNA from yeast depends on the yeast strain. In case of *Yarrowia lipolytica* a modified *S. cerevisiae* protocol has been used.
1. Inoculate 20 ml YPD in a 100 ml shake flask and ferment at 30° C. O.N.
2. Spin 5' at 5000 rpm.
3. Remove supernatant and resuspend cells in 400 µl 0.9 M Sorbitol, 0.1 M EDTA pH 7.5, 14 mM β-mercaptoethanol.
4. Add 100 µl Novozym (2 mg/ml) and incubate 30' at 37° C. (At this point one should be able to monitor spheroplast formation)
5. Spin 30" in a microfuge.
6. Remove supernatant and resuspend pellet in 400 µl TE+5 µl 10X RNase A +T (boil 10' before use).
7. Add 90 µl of fresh made 1.5 ml 0.5 M EDTA pH 8.0 (final 280 mM), 0.6 ml 2 M Tris (final 444 mM), 0.6 ml 10% SDS (final 2.2%)
8. Incubate 30' at 65° C.
9. Add 80 µl 5 M KAc. Vortex and leave on ice 30'.
10. Spin 15' at 20.000 G.
11. Transfer supernatant to a new tube. Add 1 vol. phenol/chloroform, vortex and leave at 65° C. 10'. Spin 5' at 20.000 G.
12. Transfer upper fase to a new tube and add 1 vol. chloroform. Vortex and spin. Move upper fase to a new tube. Add 3×vol. 96% EtOH. Mix carefully.
13. Spin 5' at 20.000 G.
14. Wash pellet in 70% EtOH and dry pellet at R.T.
15. Resuspend pellet gently in 250 µl of a suitable buffer.

Construction of a genomic library.

Total P01d DNA was prepared from a YPD culture. Partial Sau3A I digested DNA was fractionated on a 1% low melt agarose gel and 1–2 Kb fragments were purified by use of β-agarase. DNA fragments were ligated with pSJ1678 from which the kanamycine resistance gene was deleted as a BamHI fragment and introduced into SJ2 by electrotransformation. A library >45.000 clones was established with a vector background level <0.5%. According to the formula by Clark and Carbon (1976) this library size corresponds to a 95% probability that an arbitrary sequence is represented: $N=\ln(1,P)/\ln(1,f)$, where P equals the probability that a given unique DNA sequence is present in a collection of N transformant colonies and f is the fraction of the total genome used as a source for each fragment. The calculation relies on the assumptions that the Sau3A I restriction sites are randomly distributed throughout the genome, that all fragments ligate equally well within the size distribution of the fragments (average size=1.5 Kb), and that the P01d genome has a size of 20 Mb.

Plasmid DNA was isolated from 20 colonies and cut with HindIII. Analysis on 1% agarose gel showed a random distribution of inserts between 1 Kb and 2 Kb (data not shown).

Colony hybridization.

Coloni hybridization was performed at standard conditions. 5 replicas of the genomic library were made (3 for hybridization, 1 for plasmid DNA preparation and 1 backup). 400 bp PCR copies of the 5' end of the respective cDNA clones were used as probes.

PCR and cloning of yeast promoter sequences.

PCR was performed at standard conditions, except for primer annealing temperature, which was raised to 60° C. All products were purified prior to further use with QIAquick PCR Purification kit (QIAGEN) as recommended by the manufacturer.

PCR copies of the identified yeast promoter sequences were cloned in the expression vectors as 5'ClaI 3'BamHI fragments. These cloning sites were introduced by the PCR primers. The number of bases flanking the restriction sequences on the primers was selected as recommended by New England Biolabs®. In the Ribosomal protein S7 yeast promoter sequence, a BamHI site was present close to the 5' end. Therefore, only the sequence located downstream this site was introduced in the expression vectors. Further, an internal ClaI site was present at position , 269 from the putative translational ATG start codon. PCR editions affected by this restriction site were digested with BamHI, purified with QIAquick PCR Purification kit (QIAGEN), followed by a partial digest with ClaI. Relevant fragments were purified from 1.5% low melt agarose gel prior to ligation and transformation of MC1061. Despite repeated efforts, succesful cloning was only obtained with some of the Ribosomal protein S7 yeast promoter editions. Due to time constraints, this cloning problem was not examined any further. The different PCR copies of the Elongation factor 1 a yeast promoter sequence, and the edition of the Ribosomal protein S7 yeast promoter unaffected by the ClaI site were ClaI/BamI digested, purified with QIAquick PCR Purification kit (QIAGEN), and introduced into MC1061. Succesful cloning was verified by ClaI/BamI digest of Qiagen DNA preparations and analysis on 2% agarose gel. All the cloned PCR copies of the yeast promoters were sequenced and compared with the original genomic sequences in order to examine for misincorporations. No errors were detected.

Control vectors

Control vectors for the enzyme activity experiments were constructed on the basis of pY3- 43 kD/X1. The XPR2 yeast promoter sequences were removed as ClaI/BamHI fragments, vectors were blunt ended by Mung bean nuclease treatment, religated and amplified in MC1061. Succesful nuclease treatment was verified by restriction analysis and confirmed by sequence determination.

Enzymatic activity assays:

Cellulase I, Cellulase II, and Xylanase I:

Activity determination of Cellulase I, Cellulase II, and Xylanase I was made in liquid assays by the use of AZCL (AZurin dyed Cross Linked) substrates (MEGAZYME Australia).

Mix in an eppendorf tube:

100–145 µl optimal buffer

50 µl supernatant (in case of supernatant samples S1–S3 from xylanase I cultures only 5 µl) sample blank, standard or standard blank.

100 µl 0.4% AZCL substrate in milliQ water.

All samples are placed on ice durring the treatment. Incubate in a thermomixer at 40° C., 1200 rpm. for 15–45 minutes (Standard $OD_{620}$>0.2).

Spinn 5' at 20.000 G and measure $OD_{620}$ of the substrate-grain free supernatants. All samples are measured in duplicates. Sample and standard values are corrected for absorbance of the relevant blank. The activity value is calculated as Sample activity/Standard activity.

| Enzyme | AZCL substrate | Optimal buffer | Standard (purified native enzyme) |
| --- | --- | --- | --- |
| Cellulase I | HE-Cellulose | 0.1 M citrate/phos. pH 5.5 | 1.72 µg/µl diluted 1200 times |
| Cellulase II | HE-Cellulose | 0.1 M Tris pH 7.5 | 1.5 µg/µl diluted 200 times |
| Galactanase I | Arabinogalactan | 0.1 M citrate/phos. pH 4.5 | 2 µg/µl diluted 6000 times |
| Xylanase I | Birch-xylan | 0.1 M Tris pH 7.0 | 1.47 µg/µl diluted 30.000 times. |

Polygalacturonase I (PG I) and Lipase activity:

The enzyme activity of supernatants from both PG I and lipase cultures (chapter 5) was measured on substrate-containing plates. 20 µl supernatant from each sample was loaded in wells and the area of the clearing zone was related to the clearing zones of a titration of a known amount of the respective native enzymes.

PG I: 1.0 g agarose is added 100 ml 0.1 M citrate/phosphate buffer pH 4.5. The suspension is heated to the boiling point and 1 g Obipectin (DE 35%, NN Switzerland) prewetted in 96% EtOH is added prior discharge of 25 ml aliquots on plates. 20 µl supernatant or standard is added in wells and incubated 24 hours at 30° C. 1% MTAB (mixed alkyltrimethylammoniumbromide, Sigma®) is poured over the plates and incubates at RT untill the clearing zones are detectable.

Lipase: 2.0 g agarose is added 10 ml 1M Tris pH 9, 5 ml 2M $CaCl_2$ and 85 ml $H_2O$. The suspension is heated to the boiling point and a mixture of 0.5 ml Olive oil and 1 ml Triton X-100 is added prior discharge of 25 ml aliquots on plates. 20 µl supernatant or standard is added in wells and incubated 24 hours at 30° C.

Western blotting

SDS -PAGE electrophoresis, western blotting and immunostaining. 25 ml supernatant from the respective maximum activity per volume samples was loaded in each lane.

Hybridization

Suitable hybridization conditions for determining hybridization between an nucleotide probe and an "analogous" DNA sequence of the invention may be defined as described below. The oligonucleotide probe to be used is the DNA sequence from position −241 to −41 in SEQ ID NO 1 or from −163 to −3 in SEQ ID NO 2. The oligonucleotide probe used herein is preferably a double-stranded DNA probe.

Hybridization conditions:

Suitable conditions for determining hybridization between a nucleotide probe and a homologous DNA or RNA sequence involves presoaking of the filter containing the DNA fragments or RNA to hybridize in 5×SSC (standard saline citrate) for 10 min, and prehybridization of the filter in a solution of 5×SSC (Sambrook et al. 1989), 5×Denhardt's solution (Sambrook et al. 1989), 0.5% SDS and 100 µg/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6–13), $^{32}$P-dCTP-labeled (specific activity >1×10$^9$ cpm/µg) probe for 12 hours at ca. 45° C. The filter is then washed two times for 30 minutes in 2×SSC, 0.5% SDS at preferably not higher than 55° C., more preferably not higher than 60° C., more preferably not higher than 65° C., even more preferably not higher than 70° C., especially not higher than 75° C.

Molecules to which the oligonucleotide probe hybridizes under these conditions are detected using a x-ray film.

Media:

E. coli media:

For selective growth of transformants:

LB medium (Luria-Bertani): 1% Bacto tryptone, 0.5% Bacto yeast extract, 0.5% NaCl+relevant antibiotics as described. Growth plates are made with 2% Bactoagar.

For growth of electro-transformed cells for 1 hour, prior plating on selective medium:

Soc medium: 2% Bacto tryptone, 0.5% Bacto yeast extract, 10 mM NaCl, 2.5 mM Kcl, 10 mM $MgCl_2$, 10 mM $MgSO_4$, 20 mM glucose.

Yeast media:

Selective medium for *Yarrowia lipolytica* transformants:

Syntetic Complete medium÷Leucine 1 liter medium:

100 ml 10X Basal salt 100 ml 10X glucose (20%)

100 ml 10X Amino acids÷leucine+vitamin

Add $H_2O$ to 1000 ml. Sterile filtrate.

Growth plates are made with 1.5% agarose. Autoclave the agarose in $H_2O$ then add the remainder.

Amino acid stock solutions:

(SIGMA Cell Culture Reagent®)

| Constituent | Final mg/l |
| --- | --- |
| Adenine sulphate | 20 |
| Uracil | 20 |
| Tryptophan | 20 |
| Histidine | 20 |
| Arginine | 20 |
| Methionine | 20 |
| Tyrosine | 30 |
| Isoleucine | 30 |
| Lysine | 30 |
| Phenylalanine | 50 |
| Glutamic acid | 100 |
| Aspartic acid | 100 |

-continued

| Constituent | Final mg/l |
|---|---|
| Valine | 150 |
| Threonine | 200 |
| Serine | 400 |
| Biotin (vitamin H) | 0.05 |
| Thiamine HCl (vitamin B) | 5 |
| myo-INOSITOL | 47 |
| Pyridoxine Hcl (vitamin B6) | 1.2 |
| Pantothenic acid | 23 |

10X Basal salt:
1 liter;
66.8 g Yeast Nitrogen Base w/o amino acids (Difco), 100 g Succinic acid, 60 g NaOH. Add $H_2O$ to 1 liter and sterile filtrate.
Inducing medium for XPR2 based *Yarrowia lipolytica* transformants:
XPR2 optimal medium (a modification of the YPDm media (Nicaud, J. M. et al 1989)):
0.1% glucose
0.2% (w/v) Yeast Extract
10% (w/v) Proteose Peptone (DIFCO)
Bring Yeast Extract and Proteose Peptone to solution in 50 mM $NaHPO_4$ pH 6.8. Autoclave and add the glucose. For growth plates add 1.5% agar before autoclavation.
YP medium (per 1): 20 g Bacto peptone, 10 g Bacto yeast extract.

EXAMPLES

Example 1
Construction of cDNA libraries.

A cDNA library can be considered as an image of the transcriptional activity in the cell at the growth conditions present. The aim was to identify strong yeast promoters that were active at conditions suitable for use in expression cloning. Therefore the ability of strain P01d to assimilate various carbohydrate sources was examined prior to the construction of cDNA libraries (FIG. 3). Assimilation of carbon compounds in terms of + or , has been examined for some of the first *Y. lipolytica* strains isolated (reviewed by Lodder, J. 1970) and a slight variation among the strains was observed. In the present growth experiment carbohydrates of both categories were tested.

The growth experiment (FIG. 3) clearly demonstrated that strain P01d is capable of utilizing glucose and glycerol as carbohydrate sources. The indication of weak assimilation of maltose is in agreement with the observations by Lodder. In the attempt to identify not only strong but also inducible yeast promoters, it was decided to construct cDNA libraries from both YP-glucose and -glycerol cultures. The idea was that if the presence of glucose or glycerol caused distinct patterns of induction or repression of yeast promoters (e.g. a glucose repression effect) this would appear in a comparison of sequences from the two libraries.

Example 2
Analysis of cDNA libraries.

An initial sequence determination was performed on 100 clones from each cDNA library in which 300–600 nucleotides of the 5' end of the inserts were determined. The sequence data from each library were aligned internally and to each other. In the following the cDNA library from the YP-glucose culture is refered to as L1 and the library from the YP-glycerol culture as L2.

7 different sequences from L1 were represented twice and two different sequences were represented as triplets. It turned out that one of the pairs came from identical clones which is possible due to the growth of the transformed cells for 1 hour in liquid medium prior transfer to growth plates. 14 different sequences from L2 were represented twice, of which two pairs came from identical clones. Alignment of L1 and L2 showed that several sequences from one library also were represented in the other. Four sequences of the 200 clones examined were chosen for further examination (FIG. 4): One representing the sequence observed most frequently (A), one representing the most frequently sequence observed only in L1 (B), one representing the second most observed (C), and one representing a sequence observed twice in L2 and not in L1 (D).

Example 3
Comparative measurement of transcription frequency.

The detection of a sequence in two or three copies in only one of the cDNA libraries could indicate that different yeast promoter activity was present in the YP-glucose and -glycerol media. To test this, a Northern blot analysis was performed. PCR copies of the selected cDNA sequences were hybridized to poly(A)+RNA from the YP-glucose and -glycerol cultures respectively. If the frequency of the different cDNA sequences reflects the quantity of the corresponding transcripts, unequal intensity of signals could be expected when probes based on the L1.45 or L2.17 sequences were used.

The intensity of the signals does not differ in any case, independently of the origin of the poly(A)+RNA, this was not observed at shorter exposure either. These data indicates that no significant repression of transcription has taken place concerning the sequences examined, either in the presence of glucose or glycerol in the medium.

Example 4
Copy number analysis.

A high frequency of a specific sequence reflects the presence of a strong yeast promoter. This is of course quite a simplification. A high frequency could also be caused by a high mRNA stability or a high copy number of the gene. If all these copies were actively transcribed, the yeast promoter strength in terms of sequence frequency would be correspondingly low. In order to examine for copy number on the genome of the selected genes a Southern blot analysis was carried out.

It appears, that the probes based on the L1.41 (A), L1.45 (B) or L2.17 (D) sequences, hybridize at one or two areas on the membrane, depending on the enzymes used. Sequence determination of is the entire cloned cDNA of L1.41 and L2.17 (see later) showed that in the case of L1.41, both a HindII site and a KpnI site was present in the structural gene, and in case of L2.17 a KpnI site was present. A PCR copy of the L1.45 sequence was digested with the enzymes employed in the Southern analysis. Electrophoresis on agarose gel showed that an internal KpnI site was present (data not shown). This strongly indicate that the P01d genome contains only one copy of both L1.41, L1.45 and L2.17.

The L2.7 based probe hybridize at several distinct areas of the membrane. Digest of a PCR copy of the L2.7 sequence with the employed enzymes did not reveal an internal presence of these sites (data not shown). This show that the L2.7 sequence is present in several copies in the P01d genome. For this reason no attempt was made to identify and test the yeast promoter matching the L2.7 sequence.

Example 5
Identification of putative yeast promoter sequences by colony hybridization.

To identify the yeast promoters matching the strongly expressed transcripts, a P01d genomic library was established. 1–2 Kb Sau3A I digested P01d fragments were cloned in BamHI digested pSJ1678 (FIG. 2). 45.000 transformants were obtained corresponding to a 95% probability of an arbitrary sequence is represented. Prior coloni hybridization, PCR copies of L1.41, L1.45 and L2.17 were digested with Sau3A I. Analysis on agarose gel showed a significant reduction in fragment size (data not shown), due to the presence of internal Sau3A I sites. In order to increase the probability of identifying sequences located upstream the ATG start codon of the selected genes, 400 bp PCR copies of the 5' end of the selected cDNA sequences were used as probes.

Colony hybridization resulted in one positive for each probe used. Unfortunately, the positive corresponding to L1.45 was lost during the process of isolating the positives. HindIII digest showed that the clones responding to the L1.41 and L2.17 based probes contained inserts of approximately 1000 and 1500 bp, respectively. Sequence determination of the positive inserts was not possible when present in the pSJ1678 background and hence the insert were recloned in pUC19 prior to sequencing.

Example 6
Sequence determination of the L1.41 related genome and cDNA sequence.

The 915 bp L1.41 related genomic DNA was sequenced at both strands as illustrated in FIG. 5.

Alignment of the L1.41 related genomic DNA with the corresponding cDNA revealed a 549 bp overlap between 3' genomic DNA and 5' cDNA, corresponding to a 366 bp sequence in the genomic DNA located upstream the cDNA sequence (FIG. 6.) The sequence in FIG. 6 is the same as shown in SEQ ID NO 1.

The nucleotide sequence and the deduced amino acid sequence of the L1.41 cDNA is presented in FIG. 7. The sequence in FIG. 6 is the same as shown in SEQ ID NO 3. The 1500 bp cDNA clone contains a 1380 bp open reading frame initiated with an ATG codon 41 bp downstream the 5' terminal nucleotide, and terminated with a TAA stop codon 1421 bp downstream the 5' terminal nucleotide, thus predicting a 460-residue polypeptide of 50065 Da. The open reading frame is preceded by a 40 bp 5'-noncoding region and followed by a 60 bp 3'-noncoding region and a poly(A) tail.

An initial FastA search (Pearson and Lipman, 1988) on the GenEMBL database showed significant similarity of the L1.41 cDNA sequence to the translation elongation factor EF-1a gene (TEF) of various sources, e.g. *Arxula adeninivorans, Neurospora crassa* and *Saccharomyces cerevisiae* (see appendix II).

GAP alignments (Needleman and Wunsch, 1970) were made with the complete L1.41 cDNA sequence aligned to the TEF gene sequences of yeasts *A. adeninivorans* and *S. cerevisiae*. 83.8 and 76.4 percent similarity was observed, respectively.

At the amino acid level a BLASTX search (Altschul et al, 1990), on the swissprot database, showed as much as 91 percent identity to the elongation factor 1a of *A. gossypii*. To the corresponding genes of *C. albicans, A. adeninivorans* and *S. cerevisiae* 90, 90 and 89 percent identity was observed, respectively.

The elongation factor 1a plays an essential role in protein synthesis in eukaryotic cells by binding the amino-acyl tRNA to the ribosomes in exhange for the hydrolysis of GTP.

Example 7
Sequence determination of the L2.17 related genome and cDNA sequence.

The 1435 bp L2.17 related genomic DNA was sequenced at both strands.

The relevant part of the nucleotide sequence of the L2.17 genomic DNA is shown in FIG. 8. The sequence in FIG. 8 is the same as shown in SEQ ID NO 2.

Alignment of the L2.17 related genomic DNA with the corresponding cDNA showed that 759 bp of the genomic sequence was located upstream the 5' end of the cDNA sequence. Further, the alignment strongly indicated the presence of an intron of 165 nucleotides: A 16 bp sequence in the genomic DNA (position ,2–+14), including the putative ATG start codon, matched perfectly with a sequence located in the 5' end of the cDNA sequence. There was no homology between the genomic DNA and the cDNA in the intervening sequence.

The 16 bp genomic sequence was followed by a 5' splice site consensus sequence—GTGAGT (FIG. 8) at position 15–20. A 3' splice site consensus sequence—CAG (position 177–179)—was present in the 3' end of the 165 nucleotide intron, and an internal consensus sequence for lariat formation—TA$_3$CTAAC (position 165–173) was present just upstream the 3' consensus sequence. These intron processing signals are very similar to those that define introns in other organisms and the signals present in the intron of the pyruvate kinase-encoding gene (PYK) of *Y. lipolytica* (table II).

TABLE II

Consensus intron processing signals from several species and the signals of the *Y. lipolytica* PYK gene intron.*

| | 5' splice site | Internal conserved sequence | 3' splice site |
|---|---|---|---|
| Higher eukaryotes | GGT A/G AGT | CT A/G A T/C | TAG |
| *S. pombe* | GGTA - | CT A/G A | T/A AG |
| *N. crassa* | - GTA - | T - CTAAC | T/C AG |
| *S. cerevisiae* | GGTATGT | TACTAAC | T/C AG |
| *Y. lipolytica* PYK intron | GGTGAGT | TACTAAC | CAG |
| *Y. lipolytica* L2.17 intron | GTGAGT | TA$_3$CTAAC | CAG |

*Y. lipolytica* L2.17 splice sites and signals shown along with the corresponding consensus signals from other organisms and the *Y. lipolytica* PYK gene. Consensus sequences of higher eukaryotes, *S. pombe, N. crassa, S. cerevisiae* (Hindley and Phear, 1984; Kaufer at al, 1985). *Y. lipolytica* PYK gene (Strick et al, 1992).

As described earlier, it can be quite difficult to predict the transcription initiation site on the basis of consensus sequence data alone. In case of the TEF gene yeast promoter sequence, the presence of a CT rich sequence pointed at a single probable site. In case of the L2.17 genomic sequence, several initiation sites seems possible:

Four initiation consensus sequences are located between the putative TATA boxes (position ,201–,190) and the ATG start codon (see FIG. 8).

The fact that the cDNA sequences represented by L2.17 (L2.17 and L2.32 FIG. 4) both have their 5' end very close to the ATG start codon could indicate that they represent almost full length cDNA clones. This assumption is further supported by the presence of two transcription initiation consensus sequences just upstream the 5' end of the cDNA sequence.

The assumption of a transcriptional start site just upstream the ATG start codon disagree with the observation of an average leader sequence length in yeast of 52 bp (reviewed by Yoon and Donahue 1992). Further, this position of the transcription initiation sites is far out of the range of the transcription initiation window (40–120 bp downstream the ,201–,190 TATA boxes).

The existence of several possible transcription initiation sites was examined further in a yeast promoter deletion analysis (see below).

The L2.17 cDNA was sequenced at both strands. The nucleotide sequence and the deduced amino acid sequence of the L2.17 cDNA is presented in FIG. 9. The sequence in FIG. 9 is the same as shown in SEQ ID NO 4.

The 853 bp cDNA clone contains a 780 bp open reading frame initiated with an ATG codon 3 bp downstream the 5' terminal nucleotide, and is terminated with a TAA stop codon 783 bp downstream the 5' terminal nucleotide, thereby predicting a 260-residue polypeptide of 29193 Da. The open reading frame is preceded by a 2 bp 5'-noncoding region and followed by a 49 bp 3'-noncoding region and a poly(A) tail.

A FastA search (Pearson and Lipman, 1988) on the GenEMBL database showed similarity of the L2.17 cDNA sequence to the ribosomal protein S7 of S. cerevisiae and the corresponding ribosomal protein S4 of e.g. D. melanogaster and H. sapiens.

GAP alignments (Needleman and Wunch, 1970) showed 69.2 percent similarity to a ribosomal protein S4 cDNA sequence of D. melanogaster and 68.5% similarity to exon 1 and exon 2 of the S. cerevisiae ribosomal protein S7.

At the amino acid level a BLASTX search (Altschul et al, 1990), on the swissprot database, showed 82 percent identity to the ribosomal protein S7 of S. cerevisiae, 74 percent identity to the ribosomal protein S4 of D. melanogaster and 72 percent identity to the ribosomal protein S4 of M. musculus and H. sapiens.

The ribosomal protein S7 is the largest protein of the 40 S subunit and is essential for growth (Synetos et al 1992).

Example 8

Strategy for deletion analyses of the cloned yeast promoters.

A detailed analysis of the function of a yeast promoter involves sequence deletion studies as well as DNA/protein and protein/protein interaction analyses.

Figure 10:
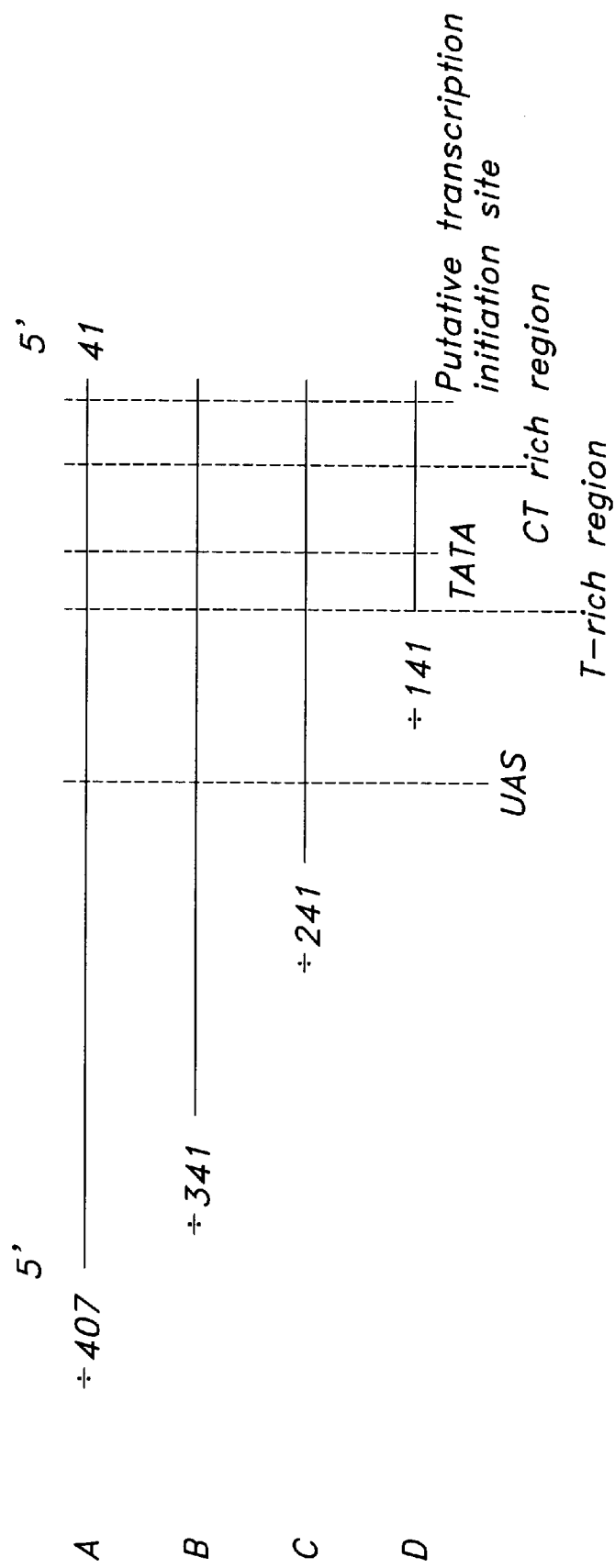

Elongation factor 1_a (TEF) yeast promoter deletions:

The strategy used for deletion studies of the TEF gene yeast promoter sequence (SEQ ID No 1) is shown in FIG. 10. The 3' terminal nucleotide of the yeast promoter sequence was defined to be equal, to the last nucleotide in the 5' part of the genomic sequence that was not represented in the cDNA sequence. This definition is in agreement with the position of the putative transcription initiation site, except for the presence of additional 12 bp located downstream the putative transcription initiation site. All editions of the TEF gene yeast promoter sequence were cloned as ClaI/BamHI fragments in pY5 expression vectors carrying cellulase II or xylanase I as reporter genes (see table I. and FIG. 2). The yeast promoter sequences were cloned in the expression vectors as PCR copies, in which the 5° ClaI site and the 3' BamHI sites were introduced by the PCR primers.

The deletion study shown that the DNA sequence from position –241 to position –41 in SEQ ID No 1 comprise the essential element for yeast promoter activity.

Figure 11:
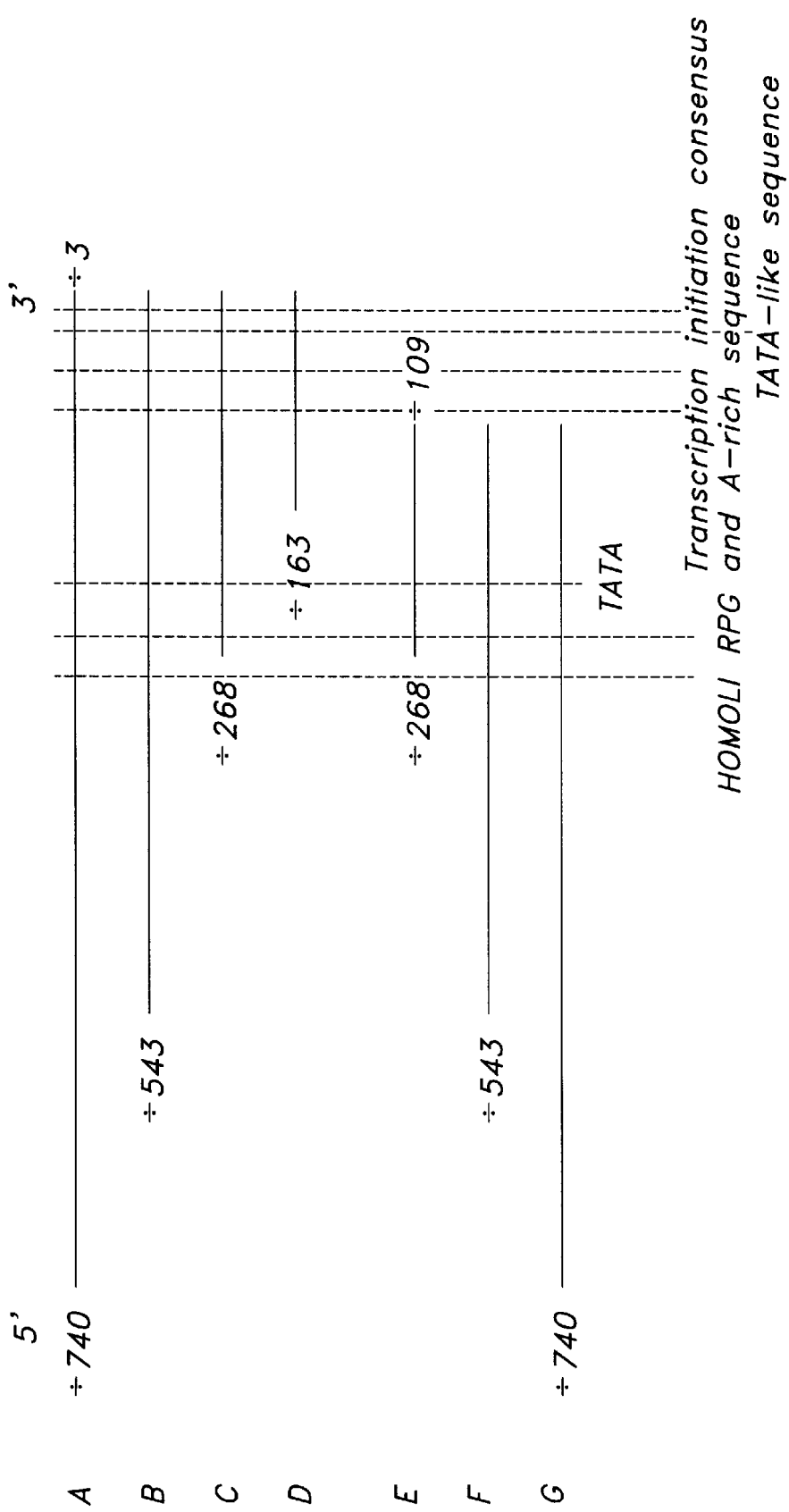
Figure 12A:
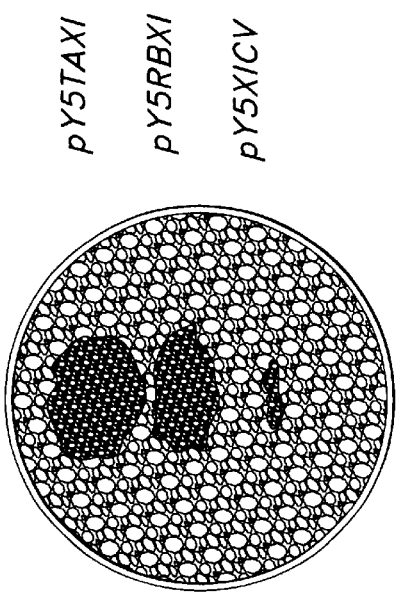
Figure 12B:
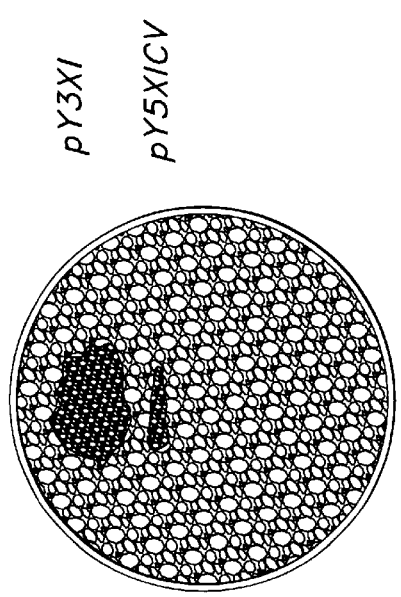
Figure 12C:
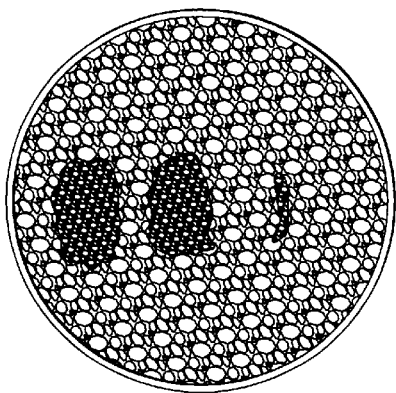
Figure 12D:
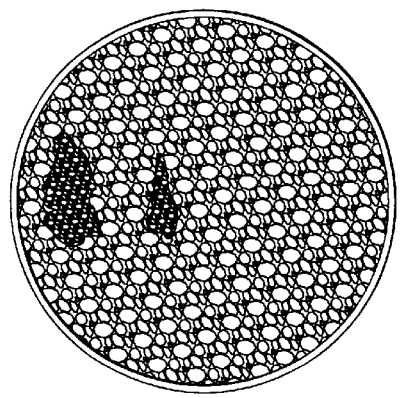

Ribosomal protein S7 yeast promoter deletions:

The planned strategy for deletion analysis of the Ribosomal protein S7 yeast promoter sequence (SEQ ID No 2) is shown in FIG. 11. Due to the problems with identification of a single probable transcription initiation site, 5' deleted editions with two different 3' ends (position ,3 and ,109) were introduced to the expression vectors. All editions of the ribosomal protein S7 yeast promoter sequence were cloned as ClaI/BamHI fragments in pY5 expression vectors carrying cellulase II or xylanase I as reporter genes (see table I. and FIG. 2). Editions affected by the internal ClaI site were prepared by partial ClaI digest as described earlier. Successful cloning was only obtained for B, D and F (FIG. 11). The yeast promoter sequences were cloned in the expression vectors as PCR copies, in which the 5° ClaI site and the 3' BamHI sites were introduced by the PCR primers.

The deletion study shown that the DNA sequence from position –163 to position –3 in SEQ ID No 2 comprise the essential element for yeast promoter activity.

Example 9

Comparative yeast promoter activity studies.

The expression vectors based on the yeast promoter sequences of the invention were tested with regard to their suitability as expression cloning tools. The activity level of the yeast promoters was examined both when P01d transformants were grown on selective substrate-containing plates, and when transformants were grown in selective liquid medium. Finally the test gene products were examined in a Western blot analysis. As a consequence of the Northern blot analysis results, transformants containing either of the new yeast promoters were grown on/in media in which glucose was used as the carbohydrate source.

Activity on growth plates.

The activity level of the yeast promoters of the invention was initially tested qualitatively, by growth of P01d transformants on selective substrate-containing plates (FIG. 12. A and B). Only transformants that include the "full length" editions of the cloned yeast promoters are shown (TEF gene yeast promoter=pY5TA43 kD and pY5TAX1, Ribosomal protein S7 yeast promoter=pY5RB43 kD and pY5RBX1). P01d transformed with the corresponding expression vectors based on the XPR2 yeast promoter, grown on XPR2 optimal medium substrate-containing plates, are shown in FIG. 12. C and D. The experiment can be considered as an imitation of a screening event.

The growth plate activity experiment show that the new yeast promoters are very effective as screening tools in case of the tested reporter genes. Even in the HE-cellulose substrate assay (which is known to be less sensitive than the xylan substrate based assay) a significant degradation is seen, contrary to the XPR2 yeast promoter based HE-cellulose substrate degradation. As seen, neither of the enzymes were expressed at a detectable level when present in the control vector constructs.

References

Altschul, S. F., Gish, W., Miller, W., Myers, E. W. and Lipman, D. J. (1990) Basic local alignment search tool. J. Mol. Biol. 215: 403–410.

Christensen, T., Wøldike, H., Boel, E., Mortensen, S. B., Hjortshøj, K., Thim, L. and Hansen, M. T. (1988) High level expression of recombinant genes in A. oryzae. Biotechnology 6: 1419–1422.

Dalbøge, H., Heldt-Hansen, H. P. (1994) A novel method for efficient expression cloning of fungal enzyme genes. Mol. Gen. Genet. 243: 253–260.

Davidow, L. S., Apostolakis, D., O'Donnell, M. M., Procter, A. R., Ogrydziak, D. M., Wing, R. A., Stasko, I. and DeZeeuw, J. R. (1985) Integrative transformation of the yeast Yarrowia lipolytica. Curr. Genet. 10: 39–48.

Davidow, L. S., Franke, A. E. and DeZeeuw, J. R. (1987 a) Eur. Patent Application 220864.

Davidow, L. S., O'Donnell, M. M., Kaczmarek, F. S., Pereira, D. A., De Zeeuw, J. R. and Franke, A. E. (1987 b) Cloning and sequenceing of the alkaline extracellular protease gene of *Yarrowia lipolytica*. J. Bacteriol. 169: 4621–4629.

Fournier, P., Guyaneux, L., Chasles, M., Gaillardin, C. (1991) Scarcity of ars sequences isolated in a morphogenesis mutant of the yeast *Yarrowia lipolytica*. YEAST. 7: 25–36.

Fournier, P., Abbas, A., Chasles, M., Kudla, B., Ogrydziak, D. M., Yaver, D., Xuan, J. -W., Peito, A., Ribet, A. -M., Feynerol, C., He, F., Gaillardin, C. (1993) Colocalization of centromeric and replicative functions on autonomously replicating sequences isolated from the yeast *Yarrowia lipolytica*. Proc. Natl. Acad. Sci. USA. 90: 4912–4916.

Gubler, U. and Hoffman, B. J. (1983) A simple and very effective method for generating cDNA libraries. Gene. 25: 263–269.

Needleman, S. B. and Wunsch, C. D. (1970) A general method applicable to the search for similarities in the amino acid sequence of two proteins. J. Mol. Biol. 48: 443–453.

Ogrydziak, D. M. and Mortimer, R. K. (1977) Genetics of extracellular protease production in *Saccharomycopsis lipolytica*. Genentics. 87: 621–632.

Ogrydziak, D. M., Bassel, J., Contopoulou, R. and Mortimer, R. (1978) Development of genetic techniques and the genetic map of the yeast *Saccharomycposis lipolytica*. Mol. Gen. Genet. 163: 229–239.

Ogrydziak, D. M. and Scharf, S. J. (1982) Alkaline extracellular protease produced by *Saccharomyces lipolytica* CX161-1B.J. Gen. Microbiol. 128: 1225–1234.

Ogrydziak, D. M. (1988) Development of genetic maps of non-conventional yeasts. J. Basic Microbiol. 28: 185–196.

Ota, Y., Oikawa, S., Morimoto, Y. and Minoda, Y. (1984) Nutritional factors causing mycelial development of *Saccharomycopsis lipolytica* Agr. Biol. Chem. 48: 1933–1939.

Pearson, W. R. and Lipman, D. J. (1988) Improved tools for biological sequence analysis. Proc. Natl. Acad. Sci. USA. 85: 2444–2448.

Raleigh, E. A., Murray, N. E., Revel, H., Blumenthal, R. M., Westaway, D., Reith, A. D., Rigby, P. W. J., Elhai, J. and Hanahan, D. (1988) MrcA and McrB restriction phenotypes of some *E. coli* strains and implications for gene cloning. Nucleic Acid Research. 16: 1563–1575.

Sambrook, J., Fritsch, E. F. and Maniatis, T. (1989) Molecular cloning: a laboratory manual. 2nd ed. cold spring Harbor Laboratory Press, Cold Spring Harbor, N.Y.

Strick, C. A., James, L. C., O'Donnell, M. M., Gollaher, M. G. and Franke, A. E. (1992) The isolation and characterization of the pyruvate kinase-encoding gene from the yeast *Yarrowia lipolytica*. Gene. 118: 65–72.

Synetos, D., Dabeva, M. D. and Warners, J. R. (1992) The yeast ribosomal protein S7 and its genes. J. Biol. Chem. 267: 3008–3013.

Wertman, K. F., Wyman, A. R. and Botstein, D. (1986) Host/vector interactions which affect the viability of recombinant phage lambda clones. Gene. 49: 253–262

---

What is claimed is:

1. A yeast promoter, comprising
   a) positions 1–366 of the DNA sequence of SEQ ID NO:1, or
   b) a DNA sequence comprising at least 90% homology with the DNA sequence of a), or
   c) a DNA sequence which hybridizes with the same the complement of the DNA sequence of a) under the following hybridization conditions: prehybridization in a solution of 5×SSC, 5×Denhardt's solution, 0.5% SDS and 100 µl/ml denatured DNA, followed by hybridization in the same solution for 12 hours at about 45° C., followed by two 30 minute washes in 2×SSC, 0.5% SDS at 55–65° C.

2. The yeast promoter of claim 1, wherein the DNA sequence in a) comprises positions 166–366 of SEQ ID NO:1.

3. The yeast promoter of claim 1, wherein the yeast is a strain of *Yarrowia lipolytica*.

4. The yeast promoter of claim 1, wherein the yeast promoter is a promoter of the EF-1a protein.

5. A yeast promoter, comprising
   a) positions 218–758 of SEQ ID NO:2, or
   b) a DNA sequence comprising at least 90% homology with the DNA sequence of a), or
   c) a DNA sequence which hybridizes with the the complement of the DNA sequence of a) under the following hybridization conditions: prehybridization in a solution of 5×SSC, 5×Denhardt's solution, 0.5% SDS and 100 µl/ml denatured DNA, followed by hybridization in the same solution for 12 hours at about 45° C., followed by two 30 minute washes in 2×SSC, 0.5% SDS at 55–65° C.

6. The yeast promoter of claim 5, wherein the DNA sequence in a) comprises positions 598–758 of SEQ ID NO:2.

7. The yeast promoter of claim 5, wherein the yeast is a strain of *Yarrowia lipolytica*.

8. The yeast promoter of claim 5, wherein the yeast promoter is a promoter of the ribosomal protein S7 gene.

9. An expression vector comprising the yeast promoter of claim 1.

10. An expression cloning method in yeast, comprising
    (a) cloning, in the expression vector of claim 9, a DNA library from an organism suspected of producing one or more proteins of interest,
    (b) transforming a yeast host cell with the vector of step (a),
    (c) culturing the transformed host cell of step (b) under suitable conditions to express any protein of interest encoded by a clone in the DNA library, and
    (d) screening for positive clones by determining any activity of a protein expressed in step (c).

11. The method of claim 10, wherein yeast host cell is a strain of *Yarrowia lipolytica*.

12. The expression vector of claim 9, further comprising a DNA sequence encoding a protein of interest.

13. A yeast host cell transformed with the recombinant expression vector of claim 9.

14. A process for producing a protein in yeast comprising culturing a yeast host cell transformed with the recombinant expression vector of claim 12 under conditions permitting production of the protein of interest, and recovering the resulting protein from the culture.

15. The process of claim 14, wherein the yeast host cell is a strain of *Yarrowia lipolytica*.

* * * * *